United States Patent

Audia et al.

[11] Patent Number: 5,846,982
[45] Date of Patent: Dec. 8, 1998

[54] INHIBITION OF SEROTONIN REUPTAKE

[75] Inventors: James E. Audia; Daniel J. Koch; Thomas E. Mabry; Jeffrey S. Nissen; Vincent P. Rocco, all of Indianapolis; Yao-Chang Xu, Fishers, all of Ind.

[73] Assignee: Eli Lilly and Company, Indianapolis, Ind.

[21] Appl. No.: 862,208

[22] Filed: May 22, 1997

Related U.S. Application Data

[60] Provisional application No. 60/019,751 Jun. 14, 1996.

[51] Int. Cl.⁶ ............ A61K 31/43; A61K 31/44; C07D 409/04; C07D 401/04
[52] U.S. Cl. ............ 514/318; 514/324; 546/193; 546/202
[58] Field of Search .................. 546/193, 202; 514/318, 324

[56] References Cited

U.S. PATENT DOCUMENTS

| | | | |
|---|---|---|---|
| 3,974,280 | 8/1976 | Bernasconi | 514/324 |
| 4,195,081 | 3/1980 | Nedelec et al. | 514/339 |
| 4,196,209 | 4/1980 | Dumont et al. | 514/323 |
| 4,232,031 | 11/1980 | Dument et al. | 514/339 |
| 4,278,677 | 7/1981 | Nedelec et al. | 514/339 |
| 4,324,790 | 4/1982 | Guillaume et al. | 514/323 |
| 4,333,939 | 6/1982 | Guillaume et al. | 514/339 |
| 5,409,940 | 4/1995 | Hulkenberg et al. | 514/337 |
| 5,521,197 | 5/1996 | Audia | 514/323 |
| 5,532,240 | 7/1996 | Nakao et al. | 514/254 |
| 5,576,321 | 11/1996 | Krushinski, Jr. et al. | 514/255 |

FOREIGN PATENT DOCUMENTS

| | | |
|---|---|---|
| 0 708 102 A | 4/1996 | European Pat. Off. . |
| 0 714 894 A | 6/1996 | European Pat. Off. . |
| 0 747 049 | 12/1996 | European Pat. Off. . |
| 2486081 | 1/1992 | France . |
| 2456246A | 6/1975 | Germany . |
| WO 95 33721 A | 12/1995 | WIPO . |

OTHER PUBLICATIONS

Chemical Abstracts, vol. 83(19),abst.No. 163,998J,Nov. 10, 1975.
Malleron, J., J. Med. Chem. 1993, vol. 36, pp. 1194–1202.
Redrobe, J., Euro, J. Pharmacol., Dec. 30, 1996, vol. 318, pp. 213–220.

*Primary Examiner*—Alan L. Rotman
*Attorney, Agent, or Firm*—Robert D. Titus; David E. Boone

[57] ABSTRACT

This invention provides compounds and a method for the inhibition of serotonin reuptake in mammals.

6 Claims, No Drawings

INHIBITION OF SEROTONIN REUPTAKE

This application claims benefit of USC Provisional Application No. 60/019,751, filed Jun. 14, 1996.

BACKGROUND OF THE INVENTION

During the past two decades, the relationship between neuronal monoamines in the brain and a variety of diseases and conditions has been appreciated and investigated. The discovery of selective monoamine reuptake inhibitors has provided the medical community with exciting new tools with the potential for treatment of several physiological and psychological disorders. Reuptake inhibitors increase the levels of endogenous monoamines by inhibiting the neuronal mechanism for recovering the monoamine from the synapse without interfering with the neuronal receptors. If the reuptake inhibitor is selective for a particular monoamine, undesirable side-effects from the therapy can be reduced.

Fluoxetine, a selective inhibitor of serotonin reuptake, has gained wide acceptance as a therapy for the treatment of depression and eating disorders, and is under active investigation for the treatment of other disorders. Similarly, tomoxetine hydrochloride[(-)-N-methyl-3-(2-methylphenoxy)propanamine hydrochloride] is a selective inhibitor of norepinephrine uptake being investigated clinically for the treatment of urinary incontinence. These compounds are among many taught in U.S. Pat. Nos. 4,018,895, 4,194,009, 4,314,081 and 5,026,707 as being potent inhibitors of the uptake of various physiologically active monoamines, including serotonin, norepinephrine and dopamine.

Certain piperidinylindoles and tetrahydropyridinylindoles are known to be agonists at the serotonin 5-$HT_1$-like receptor (Baker et al., U.S. Pat. No. 5,298,520), and to have affinity for the serotonin 5-$HT_1$, 5-$HT_{1A}$, and 5-$HT_2$ receptors (Taylor et al., *Molecular Pharmacology*, 34, 42–53 (1988)). Certain piperidinylbenzothiophenes are known to be serotonin 5-$HT_2$ antagonists (Watanabe et al., *Journal of Heterocyclic Chemistry*, 30, 445 (1993)). The ability of these classes of compounds to inhibit the reuptake of serotonin, however, has heretofore not been appreciated.

SUMMARY OF THE INVENTION

The present invention provides a method for the inhibition of serotonin reuptake comprising administering to a mammal in need of such inhibition a pharmaceutically effective amount of tetrahydropyridinyl- and piperidinyl-indoles and benzothiophenes of Formula I:

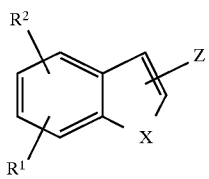

where Z is a structure of formula

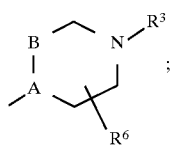

A—B is —C=CH— or —C($R^5$)—$CH_2$—;

X is S or $NR^4$;

$R^1$ is H, halo, formyl, $C_1$-$C_4$ alkyl, $C_3$-$C_6$ cycloalkyl, $C_1$-$C_4$ alkoxy, thienylmethyloxy, 4,5-dihydrothiazol-2-yl, cyano, nitro, carboxamido, trifluoromethyl or hydroxy;

$R^2$ is H or halo;

$R^3$ is H, $C_1$-$C_4$ alkyl, ($C_1$-$C_4$ alkylene)-aryl, or —$CH_2$—Y—$NR^7R^8$;

$R^4$ is H, $C_1$-$C_4$ alkyl, $C_1$-$C_5$ acyl, or phenylsulfonyl;

$R^5$ is H or OH;

$R^6$ is H or methyl;

Y is —$CH_2$— or —C(O)—;

$R^7$ is pyridinyl; and $R^8$ is H or —C(O)—($C_3$-$C_6$ cycloalkyl).

Certain compounds of formula I are novel. A further embodiment of this invention, therefore, are the optionally substituted tetrahydropyridinyl- and piperidinylbenzothiophenes of formula II:

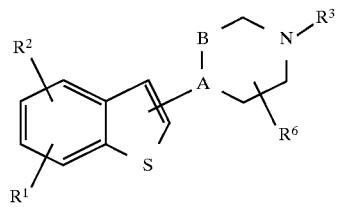

where

A—B is —C=CH— or —C($R^5$)—$CH_2$—;

$R^1$ is H, halo, formyl, $C_1$-$C_4$ alkyl, $C_3$-$C_6$ cycloalkyl, $C_1$-$C_4$ alkoxy, 4,5-dihydrothiazol-2-yl, cyano, nitro, carboxamido, trifluoromethyl or hydroxy;

$R^2$ is H or halo;

$R^3$ is H, $C_1$-$C_4$ alkyl, ($C_1$-$C_4$ alkylene)-aryl, or —$CH_2$—Y—$NR^7R^8$;

$R^5$ is H or OH;

$R^6$ is H or methyl;

Y is —$CH_2$— or —C(O)—;

$R^7$ is pyridinyl; and $R^8$ is H or —C(O)—($C_3$-$C_6$ cycloalkyl) and pharmaceutically acceptable salts and hydrates thereof.

While all of the compounds of Formula II are useful serotonin reuptake inhibitors, the compounds of Formula III, where Y, A—B and $R^1$-$R^8$ are as previously defined, are preferred:

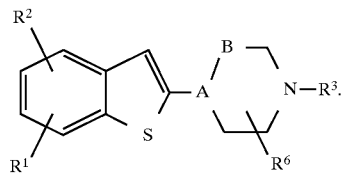

This invention also provides a pharmaceutical formulation which comprises, in association with a pharmaceutically acceptable carrier, diluent or excipient, a compound of Formula II.

DETAILED DESCRIPTION

The general chemical terms used in the formulae above have their usual meanings. For example, the term "alkyl" includes such groups as methyl, ethyl, n-propyl, isopropyl, n-butyl, isobutyl, sec-butyl, tert-butyl, and the like. The term "alkoxy" includes methoxy, ethoxy, propoxy, isopropoxy, butoxy and the like. The term "acyl" includes such groups as formyl, acetyl, propanoyl, 2-methylpropanoyl, butanoyl, 2-methylbutanoyl, 3-methylbutanoyl and 2,2-dimethylpropanoyl. The term "$C_3$–$C_6$ cycloalkyl" includes cyclopropyl, cyclobutyl, cyclopentyl and cyclohexyl. The term "halogen" includes fluoro, chloro, bromo and iodo. The term "($C_1$–$C_4$ alkylene)-aryl" is taken to be an alkylene chain of 1–4 carbon atoms terminating in a phenyl moiety or a pyrazol-4-yl moiety optionally substituted at the 1-position with $C_1$–$C_4$ alkyl, cyclopropylmethyl or phenyl.

While all of the compounds of formulae I and II are useful for the inhibition of serotonin reuptake, certain classes of the compounds are preferred. The following paragraphs describe such preferred classes.

a) X is NH;
b) X is S;
c) A—B is —C=CH—;
d) A—B is —CH—$CH_2$—;
e) $R^1$ is halogen;
f) $R^1$ is chloro;
g) $R^1$ is nitro;
h) $R^1$ is trifluoromethyl;
i) $R^1$ is at the 6-position of the indole or benzothiophene nucleus;
j) $R^1$ is at the 7-position of the indole or benzothiophene nucleus;
k) $R^2$ is hydrogen;
l) $R^2$ is halogen;
m) $R^1$ and $R^2$ are both halogen and are adjacent to each other on the indole or benzothiophene nucleus;
n) $R^3$ is H;
o) $R^3$ is $C_1$–$C_4$ alkyl;
p) $R^3$ is methyl;
q) $R^6$ is H;
r) $R^6$ is methyl;
s) X is NH and Z is attached to the 3-position of the indole nucleus;
t) X is S and Z is attached to the 2-position of the benzothiophene nucleus.

It will be understood that the above classes may be combined to form additional preferred classes.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyro-phosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

Certain compounds of the invention where $R^6$ is $CH_3$ are chiral. As such, these compounds may exist as single members of specific optical isomer pairs (a)–(d), as mixtures of these optical isomer pairs, or as racemic mixtures of these optical isomer pairs. The skilled artisan will also appreciate that isomer pairs (a) and (c) exist as diastereomers, since the alkyl moiety creates an element of asymmetry at the 4-position of the piperidine nucleus. All of these diastereomers and enantiomers are contemplated by the present invention.

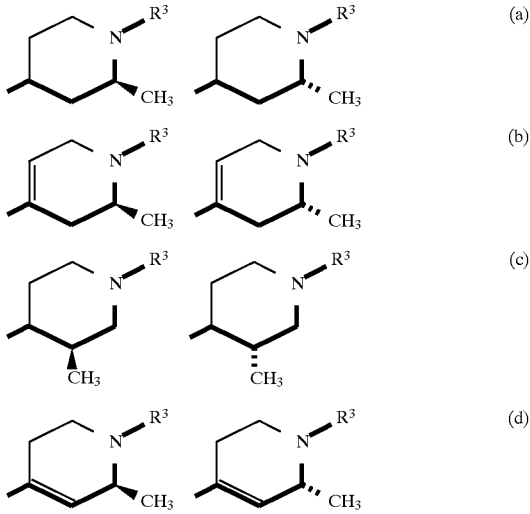

While all racemates, single enantiomers, and mixtures of enantiomers are useful serotonin reuptake inhibitors, it is preferred that the compound be a single enantiomer.

The skilled artisan will appreciate that the pure isomers may be prepared from chiral starting materials, or by fractional crystallization using chiral acids. Additionally, compounds of the invention where $R^3$ is H may be used as intermediates by introducing a chiral auxiliary, separating the diastereomers by fractional crystallization or chromatography, and then cleaving the chiral auxiliary. $R^3$ substituents could then be reintroduced, as desired, by reductive alkylation or alkylation with an appropriate reagent.

The following group is illustrative of the compounds of the present invention:

(+)-4-chloro-3-(1,3-dimethylpiperidin-4-yl) benzothiophene hydrobromide (−)-4-nitro-3-(1-isopropyl-2-methylpiperidin-4-yl) benzothiophene maleate 4-cyano-3-(1-ethylpiperidin-4-yl)benzothiophene oxalate 4-carboxamido-3-(1-ethylpiperidin-4-yl)benzothiophene phosphate 4-ethoxy-3-(1-butylpiperidin-4-yl)benzothiophene trifluoromethanesulfonate 4-ethyl-3-(piperidin-4-yl)benzothiophene p-toluenesulfonate 5-fluoro-3-(1-methylpiperidin-4-yl)benzothiophene hydrobromide
5-nitro-3-(1-isopropylpiperidin-4-yl)benzothiophene maleate
5-cyano-3-(1-ethylpiperidin-4-yl)benzothiophene oxalate
5-carboxamido-3-(1-ethylpiperidin-4-yl)benzothiophene phosphate
5-ethoxy-3-(1-butylpiperidin-4-yl)benzothiophene trifluoromethanesulfonate
5-ethyl-3-(piperidin-4-yl)benzothiophene p-toluenesulfonate
5,6-difluoro-3-(1-methylpiperidin-4-yl)benzothiophene
5-methyl-7-chloro-3-(1-methylpiperidin-4-yl)benzothiophene benzoate
5-methoxy-6-fluoro-3-(piperidin-4-yl)benzothiophene
6-fluoro-3-(1-methylpiperidin-4-yl)benzothiophene hydrobromide
6-nitro-3-(1-isopropylpiperidin-4-yl)benzothiophene maleate
6-cyano-3-(1-ethylpiperidin-4-yl)benzothiophene oxalate
6-carboxamido-3-(1-ethylpiperidin-4-yl)benzothiophene phosphate
6-ethoxy-3-(1-butylpiperidin-4-yl)benzothiophene trifluoromethanesulfonate
6-ethyl-3-(piperidin-4-yl)benzothiophene p-toluenesulfonate
7-fluoro-3-(1-methylpiperidin-4-yl)benzothiophene hydrobromide
7-nitro-3-(1-isopropylpiperidin-4-yl)benzothiophene maleate
7-cyano-3-(1-ethylpiperidin-4-yl)benzothiophene oxalate
7-carboxamido-3-(1-ethylpiperidin-4-yl)benzothiophene phosphate
7-propoxy-3-(1-butylpiperidin-4-yl)benzothiophene trifluoromethanesulfonate
7-methyl-3-(piperidin-4-yl)benzothiophene p-toluenesulfonate
4-chloro-2-(1-methylpiperidin-4-yl)benzothiophene hydrobromide
4-nitro-2-(1-isopropylpiperidin-4-yl)benzothiophene maleate
(+)-4-cyano-2-(1-ethyl-2-methylpiperidin-4-yl)benzothiophene oxalate
(−)-4-carboxamido-2-(1-ethyl-3-methylpiperidin-4-yl)benzothiophene phosphate
4-ethoxy-2-(1-butylpiperidin-4-yl)benzothiophene trifluoromethanesulfonate
4-ethyl-2-(piperidin-4-yl)benzothiophene p-toluenesulfonate
5-fluoro-2-(1-methylpiperidin-4-yl)benzothiophene hydrobromide
5-nitro-2-(1-isopropylpiperidin-4-yl)benzothiophene maleate
5-cyano-2-(1-ethylpiperidin-4-yl)benzothiophene oxalate
5-carboxamido-2-(1-ethylpiperidin-4-yl)benzothiophene phosphate
5-ethoxy-2-(1-butylpiperidin-4-yl)benzothiophene trifluoromethanesulfonate
5-ethyl-2-(piperidin-4-yl)benzothiophene p-toluenesulfonate
5,6-difluoro-2-(1-methylpiperidin-4-yl)benzothiophene
5-methyl-7-chloro-2-(1-methylpiperidin-4-yl)benzothiophene benzoate
5-methoxy-6-fluoro-2-(piperidin-4-yl)benzothiophene
6-fluoro-2-(1-methylpiperidin-4-yl)benzothiophene hydrobromide
6-nitro-2-(1-isopropylpiperidin-4-yl)benzothiophene maleate
6-cyano-2-(1-ethylpiperidin-4-yl)benzothiophene oxalate
6-carboxamido-2-(1-ethylpiperidin-4-yl)benzothiophene phosphate
6-ethoxy-2-(1-butylpiperidin-4-yl)benzothiophene trifluoromethanesulfonate
6-ethyl-2-(piperidin-4-yl)benzothiophene p-toluenesulfonate
7-fluoro-2-(1-methylpiperidin-4-yl)benzothiophene hydrobromide
7-nitro-2-(1-isopropylpiperidin-4-yl)benzothiophene maleate
7-cyano-2-(1-ethylpiperidin-4-yl)benzothiophene oxalate
7-carboxamido-2-(1-ethylpiperidin-4-yl)benzothiophene phosphate
7-propoxy-2-(1-butylpiperidin-4-yl)benzothiophene trifluoromethanesulfonate
7-methyl-2-(piperidin-4-yl)benzothiophene p-toluenesulfonate
4-chloro-3-(1-methyl-1,2,3,6-tetrahydropyridin-4-yl)benzothiophene hydrobromide
4-nitro-3-(1-isopropyl-1,2,3,6-tetrahydropyridin-4-yl)benzothiophene maleate
4-cyano-3-(1-ethyl-1,2,3,6-tetrahydropyridin-4-yl)benzothiophene oxalate
4-carboxamido-3-(1-ethyl-1,2,3,6-tetrahydropyridin-4-yl)benzothiophene phosphate
4-ethoxy-3-(1-butyl-1,2,3,6-tetrahydropyridin-4-yl)benzothiophene trifluoromethanesulfonate
4-ethyl-3-(1,2,3,6-tetrahydropyridin-4-yl)benzothiophene
5-fluoro-3-(1-methyl-1,2,3,6-tetrahydropyridin-4-yl)benzothiophene hydrobromide
5-nitro-3-(1-isopropyl-1,2,3,6-tetrahydropyridin-4-yl)benzothiophene maleate
5-cyano-3-(1-ethyl-1,2,3,6-tetrahydropyridin-4-yl)benzothiophene oxalate
5-carboxamido-3-(1-ethyl-1,2,3,6-tetrahydropyridin-4-yl)benzothiophene phosphate
5-ethoxy-3-(1-butyl-1,2,3,6-tetrahydropyridin-4-yl)benzothiophene trifluoromethanesulfonate
5-ethyl-3-(1,2,3,6-tetrahydropyridin-4-yl)benzothiophene p-toluenesulfonate
5,6-difluoro-3-(1-methyl-1,2,3,6-tetrahydropyridin-4-yl)benzothiophene
5-methyl-7-chloro-3-(1-methyl-1,2,3,6-tetrahydropyridin-4-yl)benzothiophene benzoate
5-methoxy-6-fluoro-3-(1,2,3,6-tetrahydropyridin-4-yl)benzothiophene
6-fluoro-3-(1-methyl-1,2,3,6-tetrahydropyridin-4-yl)benzothiophene hydrobromide
6-nitro-3-(1-isopropyl-1,2,3,6-tetrahydropyridin-4-yl)benzothiophene maleate
6-cyano-3-(1-ethyl-1,2,3,6-tetrahydropyridin-4-yl)benzothiophene oxalate 6-carboxamido-3-(1-ethyl-1,2,3,6-tetrahydropyridin-4-yl)benzothiophene phosphate 6-ethoxy-3-(1-butyl-1,2,3,6-tetrahydropyridin-4-yl)benzothiophene trifluoromethanesulfonate 6-ethyl-3-(1,2,3,6-tetrahydropyridin-4-yl)benzothiophene p-toluenesulfonate 7-fluoro-3-(1-methyl-1,2,3,6-tetrahydropyridin-4-yl)benzothiophene hydrobromide 7-nitro-3-(1-isopropyl-1,2,3,6-tetrahydropyridin-4-yl)benzothiophene maleate 7-cyano-3-(1-ethyl-1,2,3,6-tetrahydropyridin-4-yl)benzothiophene oxalate 7-carboxamido-3-(1-ethyl-1,2,3,6-tetrahydropyridin-4-yl)benzothiophene phosphate 7-propoxy-3-(1-butyl-1,2,3,6-tetrahydropyridin-4-yl)benzothiophene trifluoromethanesulfonate 7-methyl-3-(1,2,3,6-tetrahydropyridin-4-yl)benzothiophene p-toluenesulfonate 4-chloro-2-(1-methyl-1,2,3,6-tetrahydropyridin-4-yl)benzothiophene hydrobromide 4-nitro-2-(1-isopropyl-1,2,3,6-tetrahydropyridin-4-yl)benzothiophene maleate 4-cyano-2-(1-ethyl-1,2,3,6-tetrahydropyridin-4-yl)benzothiophene oxalate 4-carboxamido-2-(1-ethyl-1,2,3,6-tetrahydropyridin-4-yl)benzothiophene phosphate 4-ethoxy-2-(1-butyl-1,2,3,6-tetrahydropyridin-4-yl)benzothiophene trifluoromethanesulfonate 4-ethyl-2-(1,2,3,6-tetrahydropyridin-4-yl)benzothiophene p-toluenesulfonate 5-fluoro-2-(1-methyl-1,2,3,6-tetrahydropyridin-4-yl)benzothiophene formate 5-nitro-2-(1-isopropyl-1,2,3,6-tetrahydropyridin-4-yl)benzothiophene phthalate 5-cyano-2-(1-ethyl-1,2,3,6-tetrahydropyridin-4-yl)benzothiophene glycollate 5-carboxamido-2-(1-ethyl-1,2,3,6-tetrahydropyridin-4-yl)benzothiophene tartrate 5-ethoxy-2-(1-butyl-1,2,3,6-tetrahydropyridin-4-yl)benzothiophene trifluoroacetate 5-ethyl-2-(1,2,3,6-tetrahydropyridin-4-yl)benzothiophene benzenesulfonate 5,6-difluoro-2-(1-methyl-1,2,3,6-tetrahydropyridin-4-yl)benzothiophene 5-methyl-7-chloro-2-(1-methyl-1,2,3,6-tetrahydropyridin-4-yl)benzothiophene 4-chlorobenzoate 5-methoxy-6-fluoro-2-(1,2,3,6-tetrahydropyridin-4-yl)benzothiophene 6-fluoro-2-(1-methyl-1,2,3,6-tetrahydropyridin-4-yl)benzothiophene hydrobromide 6-nitro-2-(1-isopropyl-1,2,3,6-tetrahydropyridin-4-yl)benzothiophene maleate 6-cyano-2-(1-ethyl-1,2,3,6-tetrahydropyridin-4-yl)benzothiophene oxalate 6-carboxamido-2-(1-ethyl-1,2,3,6-tetrahydropyridin-4-yl)benzothiophene phosphate 6-ethoxy-2-(1-butyl-1,2,3,6-tetrahydropyridin-4-yl)benzothiophene trifluoromethanesulfonate 6-ethyl-2-(1,2,3,6-tetrahydropyridin-4-yl)benzothiophene toluenesulfonate 7-fluoro-2-(1-methyl-1,2,3,6-tetrahydropyridin-4-yl)benzothiophene hydrobromide 7-nitro-2-(1-isopropyl-1,2,3,6-tetrahydropyridin-4-yl)benzothiophene maleate 7-cyano-2-(1-ethyl-1,2,3,6-tetrahydropyridin-4-yl)benzothiophene oxalate 7-carboxamido-2-(1-ethyl-1,2,3,6-tetrahydropyridin-4-yl)benzothiophene phosphate 7-propoxy-2-(1-butyl-1,2,3,6-tetrahydropyridin-4-yl)benzothiophene trifluoromethanesulfonate 7-methyl-2-(1,2,3,6-tetrahydropyridin-4-yl)benzothiophene p-toluenesulfonate 4-chloro-3-(1-methylpiperidin-4-yl)-1H-indole hydrobromide 4-nitro-3-(1-isopropylpiperidin-4-yl)-1H-indole maleate 4-cyano-3-(1-ethylpiperidin-4-yl)-1H-indole oxalate 4-carboxamido-3-(1-ethylpiperidin-4-yl)-1H-indole phosphate 4-ethoxy-3-(1-butylpiperidin-4-yl)-1H-indole trifluoromethanesulfonate 4-ethyl-3-(piperidin-4-yl)-1H-indole p-toluenesulfonate (+)-5-fluoro-3-(1,2-dimethylpiperidin-4-yl)-1H-indole bisulfate 5-nitro-3-(1-isopropylpiperidin-4-yl)-1H-indole monohydrogenphosphate 5-cyano-3-(1-ethylpiperidin-4-yl)-1H-indole xylenesulfonate 5-carboxamido-3-(1-ethylpiperidin-4-yl)-1H-indole dihydrogenphosphate 5-ethoxy-3-(1-butylpiperidin-4-yl)-1H-indole trifluoromethanesulfonate (−)-5-ethyl-3-(2-methylpiperidin-4-yl)-1H-indole p-toluenesulfonate 5,6-difluoro-3-(1-methylpiperidin-4-yl)-1H-indole 5-methyl-7-chloro-3-(1-methylpiperidin-4-yl)-1H-indole benzoate 5-methoxy-6-fluoro-3-(piperidin-4-yl)-1H-indole 6-fluoro-3-(1-methylpiperidin-4-yl)-1H-indole hydrobromide 6-nitro-3-(1-isopropylpiperidin-4-yl)-1H-indole maleate 6-cyano-3-(1-ethylpiperidin-4-yl)-1H-indole oxalate 6-carboxamido-3-(1-ethylpiperidin-4-yl)-1H-indole phosphate 6-ethoxy-3-(1-butylpiperidin-4-yl)-1H-indole trifluoromethanesulfonate 6-ethyl-3-(piperidin-4-yl)-1H-indole p-toluenesulfonate 7-fluoro-3-(1-methylpiperidin-4-yl)-1H-indole hydrobromide 7-nitro-3-(1-isopropylpiperidin-4-yl)-1H-indole maleate 7-cyano-3-(1-ethylpiperidin-4-yl)-1H-indole oxalate 7-carboxamido-3-(1-ethylpiperidin-4-yl)-1H-indole phosphate 7-propoxy-3-(1-butylpiperidin-4-yl)-1H-indole trifluoromethanesulfonate 7-methyl-3-(piperidin-4-yl)-1H-indole p-toluenesulfonate 4-chloro-2-(1-methylpiperidin-4-yl)-1H-indole hydrobromide 4-nitro-2-(1-isopropylpiperidin-4-yl)-1H-indole maleate 4-cyano-2-(1-ethylpiperidin-4-yl)-1H-indole oxalate 4-carboxamido-2-(1-ethylpiperidin-4-yl)-1H-indole phosphate 4-ethoxy-2-(1-butylpiperidin-4-yl)-1H-indole trifluoromethanesulfonate 5-fluoro-2-(1-methylpiperidin-4-yl)-1H-indole hydrobromide 5-nitro-2-(1-isopropylpiperidin-4-yl)-1H-indole maleate 5-cyano-2-(1-ethylpiperidin-4-yl)-1H-indole oxalate 5-carboxamido-2-(1-ethylpiperidin-4-yl)-1H-indole phosphate 5-ethoxy-2-(1-butylpiperidin-4-yl)-1H-indole trifluoromethanesulfonate 5-ethyl-2-(piperidin-4-yl)-1H-indole p-toluenesulfonate 5,6-difluoro-2-(1-methylpiperidin-4-yl)-1H-indole 5-methyl-7-chloro-2-(1-methylpiperidin-4-yl)-1H-indole benzoate 5-methoxy-6-fluoro-2-(piperidin-4-yl)-1H-indole 6-fluoro-2-(1-methylpiperidin-4-yl)-1H-indole hydrobromide 6-nitro-2-(1-isopropylpiperidin-4-yl)-1H-indole maleate 6-cyano-2-(1-ethylpiperidin-4-yl)-1H-indole oxalate 6-carboxamido-2-(1-ethylpiperidin-4-yl)-1H-indole phosphate 6-ethoxy-2-(1-butylpiperidin-4-yl)-1H-indole trifluoromethanesulfonate 6-ethyl-2-(piperidin-4-yl)-1H-indole p-toluenesulfonate 7-fluoro-2-(1-methylpiperidin-4-yl)-1H-indole hydrobromide 7-nitro-2-(1-isopropylpiperidin-4-yl)-1H-indole maleate 7-cyano-2-(1-ethylpiperidin-4-yl)-1H-indole oxalate 7-carboxamido-2-(1-ethylpiperidin-4-yl)-1H-indole 1phosphate 7-propoxy-2-(1-butylpiperidin-4-yl)-1H-indole trifluoromethanesulfonate 7-methyl-2-(piperidin-4-yl)-1H-indole p-toluenesulfonate 4-chloro-3-(1-methyl-1,2,3,6-tetrahydropyridin-4-yl)-1H-indole hydrobromide 4-nitro-3-(1-isopropyl-1,2,3,6-tetrahydropyridin-4-yl)-1H-indole maleate 4-cyano-3-(1-ethyl-1,2,3,6-tetrahydropyridin-4-yl)-1H-indole oxalate 4-carboxamido-3-(1-ethyl-1,2,3,6-tetrahydropyridin-4-yl)-1H-indole phosphate (+)-4-ethoxy-3-(1-butyl-2-methyl-1,2,3,6-tetrahydropyridin-4-yl)-1H-indole trifluoromethanesulfonate 4-ethyl-3-(1,2,3,6-tetrahydropyridin-4-yl)-1H-indole p-toluenesulfonate 5-fluoro-3-(1-methyl-1,2,3,6-tetrahydropyridin-4-yl)-1H-indole hydrobromide 5-nitro-3-(1-isopropyl-1,2,3,6-tetrahydropyridin-4-yl)-1H-indole maleate 5-cyano-3-(1-ethyl-1,2,3,6-tetrahydropyridin-4-yl)-1H-indole oxalate 5-carboxamido-3-(1-ethyl-1,2,3,6-tetrahydropyridin-4-yl)-1H-indole phosphate 5-ethoxy-3-(1-butyl-1,2,3,6-tetrahydropyridin-4-yl)-1H-indole trifluoromethanesulfonate 5-ethyl-3-(1,2,3,6-tetrahydropyridin-4-yl)-1H-indole p-toluenesulfonate 5,6-difluoro-3-(1-methyl-1,2,3,6-tetrahydropyridin-4-yl)-1H-indole 5-methyl-7-chloro-3-(1-methyl-1,2,3,6-tetrahydropyridin-4-yl)-1H-indole benzoate 5-methoxy-6-fluoro-3-(1,2,3,6-tetrahydropyridin-4-yl)-1H-indole (−)-6-fluoro-3-(1,2-dimethyl-1,2,3,6-tetrahydropyridin-4-yl)-1H-indole hydrobromide 6-nitro-3-(1-isopropyl-1,2,3,6-tetrahydropyridin-4-yl)-1H-indole maleate 6-cyano-3-(1-ethyl-1,2,3,6-tetrahydropyridin-4-yl)-1H-indole oxalate 6-carboxamido-3-(1-ethyl-1,2,3,6-tetrahydropyridin-4-yl)-1H-indole phosphate 6-ethoxy-3-(1-butyl-1,2,3,6-tetrahydropyridin-4-yl)-1H-indole trifluoromethanesulfonate 6-ethyl-3-(1,2,3,6-tetrahydropyridin-4-yl)-1H-indole p-toluenesulfonate 7-fluoro-3-(1-methyl-1,2,3,6-tetrahydropyridin-4-yl)-1H-indole hydrobromide 7-nitro-3-(1-isopropyl-1,2,3,6-tetrahydropyridin-4-yl)-1H-indole maleate 7-cyano-3-(1-ethyl-1,2,3,6-tetrahydropyridin-4-yl)-1H-indole oxalate 7-carboxamido-3-(1-ethyl-1,2,3,6-tetrahydropyridin-4-yl)-1H-indole phosphate 7-propoxy-3-(1-butyl-1,2,3,6-tetrahydropyridin-4-yl)-1H-indole trifluoromethanesulfonate 7-methyl-3-(1,2,3,6-tetrahydropyridin-4-yl)-1H-indole p-toluenesulfonate 4-chloro-2-(1-methyl-1,2,3,6-tetrahydropyridin-4-yl)-1H-indole hydrobromide 4-nitro-2-(1-isopropyl-1,2,3,6-tetrahydropyridin-4-yl)-1H-indole maleate 4-cyano-2-(1-ethyl-1,2,3,6-tetrahydropyridin-4-yl)-1H-indole oxalate 4-carboxamido-2-(1-ethyl-1,2,3,6-tetrahydropyridin-4-yl)-1H-indole phosphate 4-ethoxy-2-(1-butyl-1,2,3,6-tetrahydropyridin-4-yl)-1H-indole trifluoromethanesulfonate 4-ethyl-2-(1,2,3,6-tetrahydropyridin-4-yl)-1H-indole p-toluenesulfonate 5-fluoro-2-(1-methyl-1,2,3,6-tetrahydropyridin-4-yl)-1H-indole hydrobromide 5-nitro-2-(1-isopropyl-1,2,3,6-tetrahydropyridin-4-yl)-1H-indole maleate 5-cyano-2-(1-ethyl-1,2,3,6-tetrahydropyridin-4-yl)-1H-indole oxalate 5-carboxamido-2-(1-ethyl-1,2,3,6-tetrahydropyridin-4-yl)-1H-indole phosphate 5-ethoxy-2-(1-butyl-1,2,3,6-tetrahydropyridin-4-yl)-1H-indole trifluoromethanesulfonate 5-ethyl-2-(1,2,3,6-tetrahydropyridin-4-yl)-1H-indole p-toluenesulfonate 5,6-difluoro-2-(1-methyl-1,2,3,6-tetrahydropyridin-4-yl)-1H-indole 5-methyl-7-chloro-2-(1-methyl-1,2,3,6-tetrahydropyridin-4-yl)-1H-indole benzoate 5-methoxy-6-fluoro-2-(1,2,3,6-tetrahydropyridin-4-yl)-1H-indole 6-fluoro-2-(1-methyl-1,2,3,6-tetrahydropyridin-4-yl)-1H-indole hydrobromide 6-nitro-2-(1-isopropyl-1,2,3,6-tetrahydropyridin-4-yl)-1H-indole maleate 6-cyano-2-(1-ethyl-1,2,3,6-tetrahydropyridin-4-yl)-1H-indole oxalate 6-carboxamido-2-(1-ethyl-1,2,3,6-tetrahydropyridin-4-yl)-1H-indole phosphate 6-ethoxy-2-(1-butyl-1,2,3,6-tetrahydropyridin-4-yl)-1H-indole trifluoromethanesulfonate 6-ethyl-2-(1,2,3,6-tetrahydropyridin-4-yl)-1H-indole p-toluenesulfonate 7-fluoro-2-(1-methyl-1,2,3,6-tetrahydropyridin-4-yl)-1H-indole hydrobromide 7-nitro-2-(1-isopropyl-1,2,3,6-tetrahydropyridin-4-yl)-1H-indole maleate 7-cyano-2-(1-ethyl-1,2,3,6-tetrahydropyridin-4-yl)-1H-indole oxalate 7-carboxamido-2-(1-ethyl-1,2,3,6-tetrahydropyridin-4-yl)-1H-indole phosphate 7-propoxy-2-(1-butyl-1,2,3,6-tetrahydropyridin-4-yl)-1H-indole trifluoromethanesulfonate 7-methyl-2-(1,2,3,6-tetrahydropyridin-4-yl)-1H-indole p-toluenesulfonate 6-(4,5-dihydrothiazol-2-yl)-2-(1-methylpiperidin-4-yl) benzothiophene dihydrochloride 5-(4,5-dihydrothiazol-2-yl)-2-(1-methyl-1,2,3,6-tetrahydropyridin-4-yl)benzothiophene maleate 7-(4,5-dihydrothiazol-2-yl)-3-(1-methylpiperidin-4-yl) benzothiophene 4-(4,5-dihydrothiazol-2-yl)-3-(1-methyl-1,2,3,6-tetrahydro-4-yl)benzothiophene The compounds useful for the method of this invention are prepared by techniques well known to one of ordinary skill in the art. The 3-piperidinyl- and 3-(1,2,3,6-tetrahydropyridinyl)-1H-indoles useful for the method of the present invention are prepared by the method illustrated in Synthetic Scheme I. $R^2$, $R^3$ and $R^6$ are as previously defined, $R^{1'}$ is H, halo, $C_1$–$C_4$ alkyl, $C_1$–$C_4$ alkoxy, cyano, nitro, carboxamido, trifluoromethyl or benzyloxy. While most of the indoles required for the preparation of compounds useful for the method of the present invention are commercially available, they may all be prepared by the Fischer indole synthesis as described in Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985).

Synthetic Scheme I

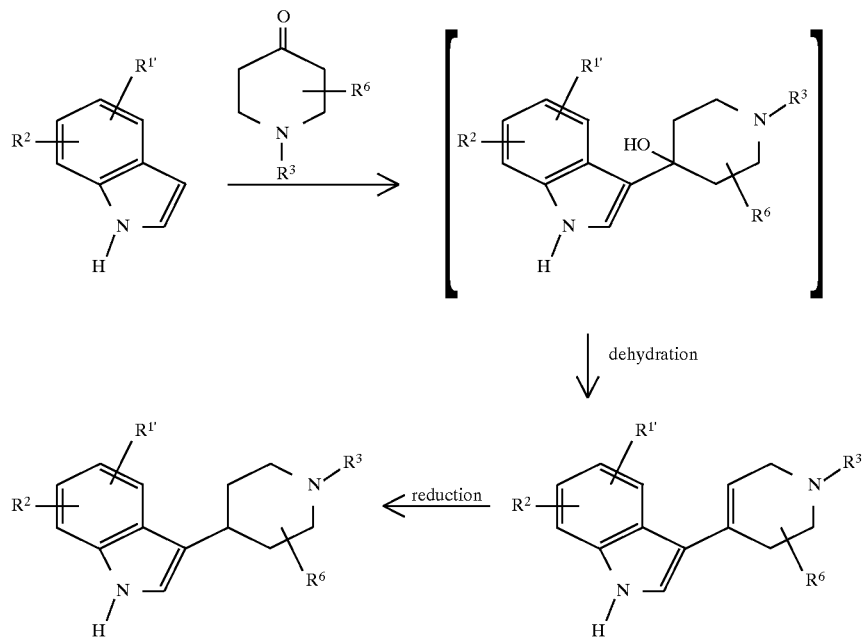

The appropriate indole is condensed with a 4-piperidone in the presence of a suitable base to initially form the corresponding 3-(4-hydroxy-1,2,3,6-tetrahydropyridin-4-yl)-1H-indoles. If desired, these may be isolated as they form and be dehydrated under standard conditions in a separate step, but they will spontaneously dehydrate to provide the corresponding 3-(1,2,3,6-tetrahydropyridin-4-yl)-1H-indoles if the reaction is allowed to continue. The reaction is performed by first dissolving an excess of the base, typically sodium or potassium hydroxide, in a lower alkanol, typically methanol or ethanol. The indole and two equivalents of the 4-piperidone are then added and the reaction refluxed for 8–72 hours. The resulting 3-(1,2,3,6-tetrahydropyridin-4-yl)-1H-indoles may be isolated from the reaction mixture by the addition of water. Compounds which precipitate may be isolated directly by filtration while others may be extracted with a water immiscible solvent such as ethyl acetate or dichloromethane. The compounds recovered may be used directly in subsequent steps or first purified by silica gel chromatography or recrystallization from a suitable solvent.

The 3-(1-substituted-1,2,5,6-tetrahydro-4-pyridinyl)-1H-indoles may be used to prepare other compounds of the invention or, if desired, may be hydrogenated over a precious metal catalyst, such as palladium on carbon, to give the corresponding 3-(piperidin-4-yl)-1H-indoles. When R or R' is bromo, a hydrogenation catalyst such as sulfided platinum on carbon, platinum oxide, or a mixed catalyst system of sulfided platinum on carbon with platinum oxide is used to prevent hydrogenolysis of the bromo substituent during reduction of the tetrahydropyridinyl double bond. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. The 3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

As an alternative to hydrogenation, the 3-(1,2,3,6-tetrahydro-4-pyridinyl)-1H-indoles may be converted to the corresponding 3-(piperidin-4-yl)-1H-indoles by treatment with triethylsilane if desired. The 3-(1-substituted-1,2,5,6-tetrahydro-4-pyridinyl)-1H-indole is dissolved in trifluoroacetic acid to which is added an excess, 1.1–10.0 equivalents, of triethylsilane. The reaction mixture is stirred at about ambient temperature for from about 1 to about 48 hours at which time the reaction mixture is concentrated under reduced pressure. The residue is then treated with 2N sodium or potassium hydroxide and the mixture extracted with a water immiscible solvent such as dichloromethane or diethyl ether. The resultant 3-(piperidin-4-yl)-1H-indole is purified by column chromatography if desired.

The 2-piperidinyl- and 2-(1,2,3,6-tetrahydropyridinyl)-1H-indoles useful for the method of the present invention are prepared by the method of Beck et al. (*Helvetica Chimica Acta*, 51(2), 260 (1968)) as illustrated in Synthetic Scheme II. $R^2$, $R^3$ and $R^6$ are as previously defined, $R^{1'}$ is H, halo, $C_1$–$C_4$ alkyl, $C_1$–$C_4$ alkoxy, cyano, nitro, carboxamido, trifluoromethyl or benzyloxy, and LG is a standard leaving group such as chloro, bromo, iodo, or trifluoromethanesulfonyloxy. The phenylhydrazines necessary as starting materials are either commercially available or may be prepared from the corresponding anilines by diazotization followed by reduction with tin(II) chloride under acidic conditions.

Synthetic Scheme II

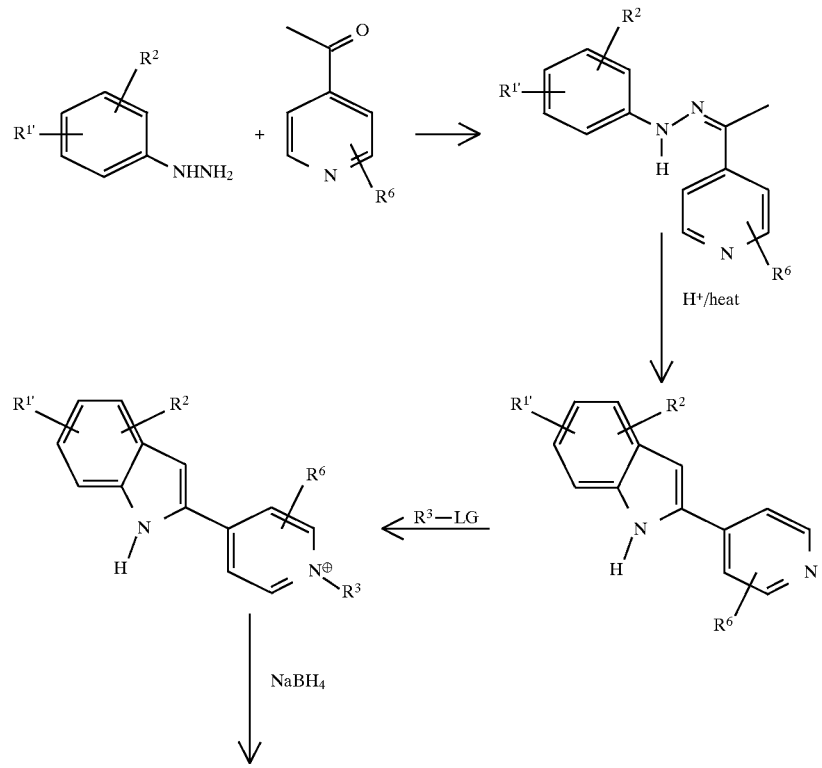

-continued
Synthetic Scheme II

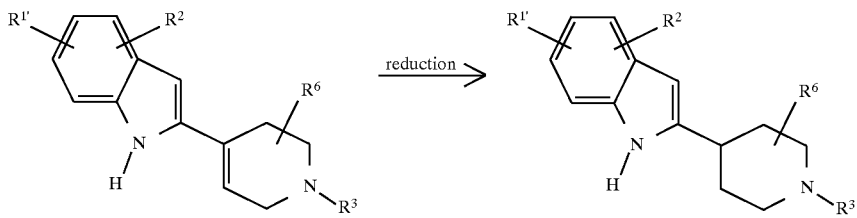

An appropriately substituted phenylhydrazine is reacted with a 4-acetylpyridine to form the corresponding phenylhydrazone. This phenylhydrazone is then subjected to standard Fischer indolization conditions (Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985)). The pyridine nitrogen of the resulting 2-(pyridin-4-yl)-1H-indole is then quaternized with an appropriate alkylating agent and the resulting quaternary ammonium salt is reduced with sodium borohydride to give the corresponding 2-(1-substituted-1,2,3,6-tetrahydropyridin-4-yl)-1H-indole. Further reduction is accomplished as described supra, with hydrogen over a platinum or palladium catalyst, or with triethylsilane under acidic conditions, to provide the desired 2-(1-substituted-piperidin-4-yl)-1H-indoles. The 2-(1-substituted-piperidin-4-yl)-1H-indoles may also be prepared directly by beginning with an appropriately substituted 4-acetylpiperidine if desired.

Alternatively, the 2-substituted-1H-indoles of the present invention may be prepared as described in Synthetic Scheme III. $R^1$, $R^2$ and $R^6$ are as previously defined, $R^{3'}$ is $C_1$–$C_4$ alkyl, or benzyl.

Synthetic Scheme III

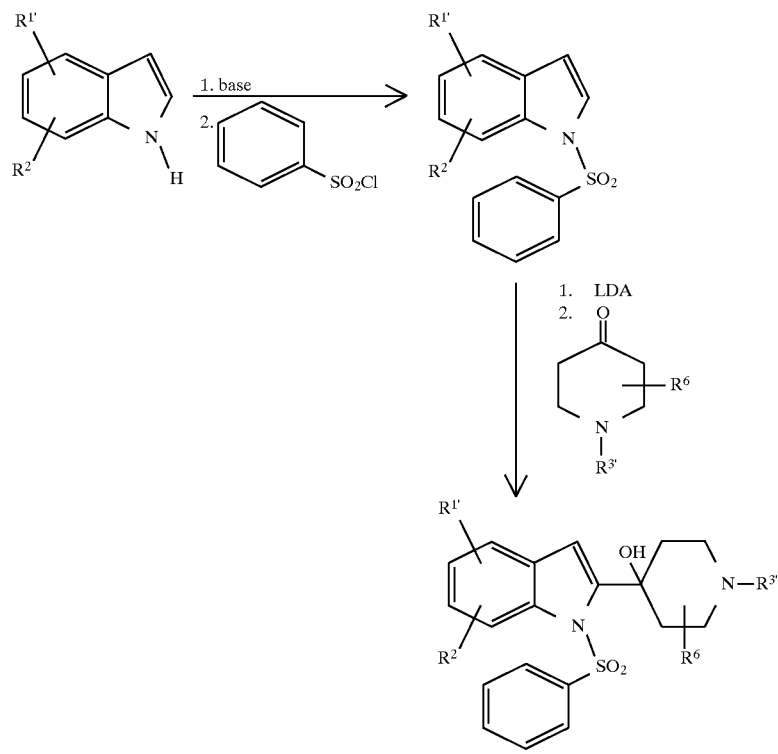

An appropriate indole is N-deprotonated and the resulting anion reacted with phenylsulfonyl chloride to provide the corresponding 1-phenylsulfonylindole. This protected indole may be purified or treated directly with an appropriate base, typically a lithium amide such as lithium diisopropylamide, and then reacted with an appropriate piperidone to provide the 1-phenylsulfonyl-2-(4-hydroxypiperidine)-1H-indoles of the present invention.

These compounds also serve as intermediates to other 2-substituted indoles of the invention.

The phenylsulfonyl group may be removed by basic hydrolysis before or after acid catalyzed dehydration of the 4-hydroxypiperidine moiety to provide the corresponding 2-(1,2,3,6-tetrahydropyridin-4-yl)-1H-indoles. The dehydration of the tertiary alcohol to prepare the desired 3-(1,2,3,6-tetrahydropyridin-4-yl)-1H-indole is accomplished by treatment with an acid in an appropriate solvent. The solvent must be capable of solvating the tertiary alcohol as well as inert to the reaction conditions. Preferred solvents are toluene and dichloromethane. The acid may be soluble in the reaction mixture or may be an acidic resin which is insoluble in the reaction mixture. Trifluoroacetic acid is a preferred soluble acid and AMBERLYST 15™ (Aldrich Chemical Company, P.O. Box 2060, Milwaukee, Wis. 53201, U.S.A.) is a preferred acidic resin. The dehydration reactions may be run at from about ambient temperature to the reflux temperature of the solvent.

Once the dehydration is complete, the reaction mixture is concentrated under reduced pressure. In those cases where an acidic resin is used, it is more convenient to remove the resin by filtration prior to concentration of the reaction mixture under reduced pressure. The residue is then dissolved in a water immiscible solvent, such as dichloromethane, and the organic solution is washed with an aqueous base such as sodium bicarbonate solution. The remaining organic phase is dried and then concentrated under reduced pressure. The residue may be used directly in other reactions, converted to an appropriate salt, crystallized or purified by chromatography as desired. These may then be hydrogenated to the corresponding piperidines as described supra.

The novel 3-piperidinyl- and 3-(1,2,3,6-tetrahydropyridinyl)benzothiophenes of the present invention are prepared by the method illustrated in Synthetic Scheme IV.

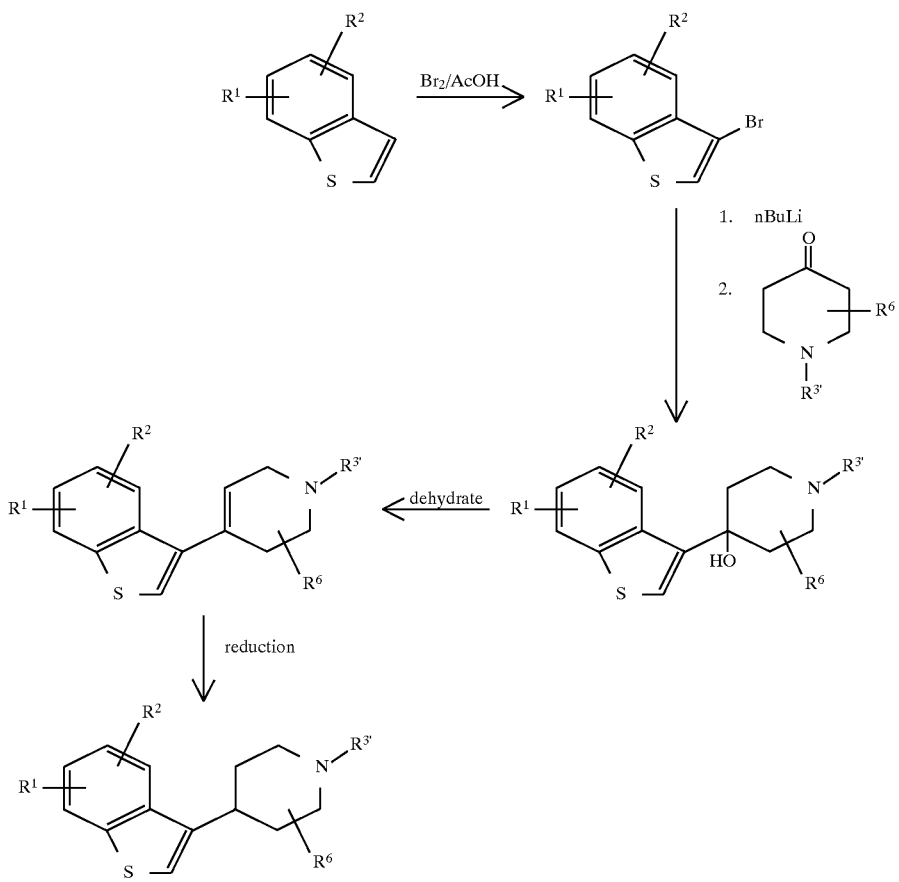

$R^1$, $R^2$ and $R^6$ are as previously defined, and $R^{3'}$ is $C_1$–$C_4$ alkyl, benzyl, or a nitrogen protecting group stable to the reaction conditions. Nitrogen protecting groups useful for these reactions are well known to the skilled artisan (Greene, *Protective Groups in Organic Synthesis*, Second Edition, Wiley Interscience, New York (1991)). Preferred protecting groups are the $C_1$–$C_4$ alkoxycarbonyl groups, such as ethoxycarbonyl and t-butyloxycarbonyl.

A suitable benzothiophene is selectively brominated with bromine in acetic acid. The reaction is typically performed at about 50° C. for about 4 hours. The volatiles are then removed under reduced pressure and the residue is subjected to an extractive workup under basic conditions. The resulting 3-bromobenzothiophene in diethyl ether is then treated with an alkyllithium, typically n-butyllithium, in the same solvent, at −78° C. After stirring at this temperature for about 1 hour, the reaction mixture is treated with an equivalent of an appropriate 4-piperidone. Once the addition of the 4-piperidone is complete, the reaction mixture is stirred at −78° C. for an additional 3 hours. It is critical to maintain the reaction mixture at this temperature to avoid equilibration of the anion to the 2-position of the benzothiophene ring. The reaction mixture is then allowed to warm to −20° C. over about 50 minutes. The reaction mixture is then quenched with saturated aqueous sodium bicarbonate and is then diluted with 1:1 hexane:di-ethyl ether. The resulting mixture is washed with brine, the organic phase dried and then concentrated under reduced pressure. The resulting tertiary alcohol may be used directly for the subsequent dehydration step as described supra, or first purified by chromatography or crystallization as appropriate. The corresponding 3-(piperidin-4-yl)benzothiophenes may be prepared by reduction of the 3-(1,2,3,6-tetrahydropyridin-4-yl) benzothiophenes prepared in this manner by the reduction conditions described supra.

The novel 2-benzothiophenes of the present invention are prepared by the method illustrated in Synthetic Scheme V. $R^1$, $R^2$, $R^{3'}$ and $R^6$ are as previously defined.

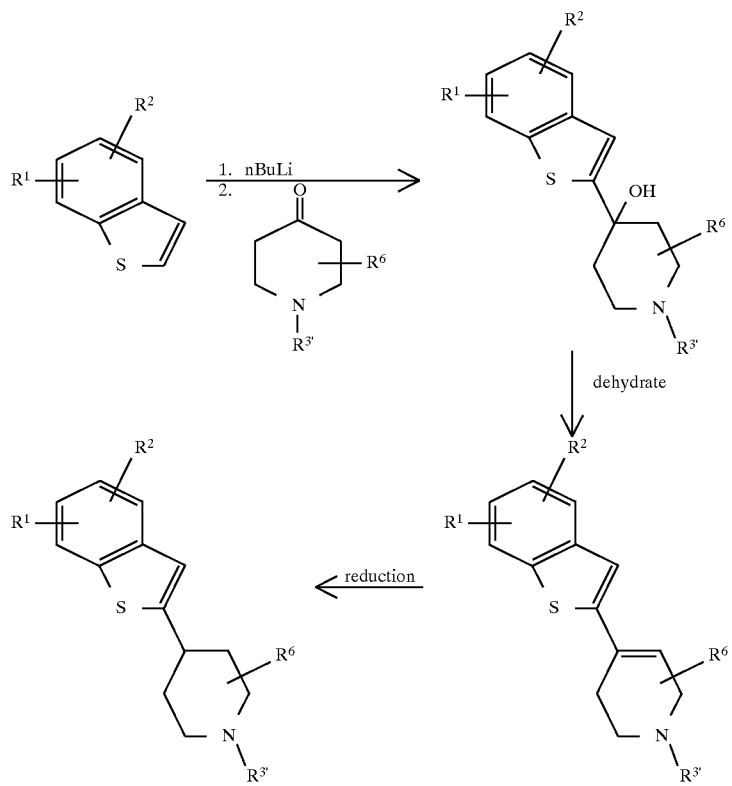

Synthetic Scheme V

An appropriate benzothiophene is treated with an alkyllithium, typically n-butyllithium, in a suitable solvent, preferably tetrahydrofuran or diethyl ether, at −78° C. After stirring at this temperature for about 1 hour, the reaction mixture is treated with an equivalent of an appropriate 4-piperidone. Once the addition of the 4-piperidone is complete, the reaction mixture is allowed to warm to about 0° C. The reaction mixture is then quenched with saturated aqueous sodium bicarbonate and is then diluted with 1:1 hexane:diethyl ether. The resulting mixture is washed with brine, the organic phase dried and then concentrated under reduced pressure. The resulting tertiary alcohol may be used directly for the subsequent dehydration step or first purified by chromatography or crystallization as appropriate. The dehydration and subsequent reduction steps are performed as described supra to prepare the desired 2-(1,2,3,6-tetrahydropyridinyl)- and 2-piperidinylbenzothiophenes respectively.

The skilled artisan will appreciate that not all of the $R^1$ and $R^2$ substituents will survive the anion chemistry described supra. The preparation of compounds containing functionality sensitive to anion chemistry may be accomplished by the use of an appropriate amino-substituted substrate. Once the anion chemistry is completed, the amino group may be diazotized and displaced under standard methods to provide the appropriate halo or cyano substituted compound. The nitrile may be hydrated to the carboxamide if desired. Additionally, the nitrile may be treated with 2-mercaptoethylamine to prepare compounds of the invention bearing the 4,5-dihydrothiazol-2-yl moiety. Furthermore, when halo is bromo or iodo, these may be treated with an alkyllithium and quenched with dimethylformamide to provide the corresponding formyl substituted compounds of the invention.

The benzothiophenes required for the preparation of the novel compounds useful for the method of the present invention are either commercially available or may be prepared by methods well known to the skilled artisan. For example, Method (a) of Synthetic Scheme VI is that of Beck et al. (*Journal of Organic Chemistry,* 37(21), 3224 (1972)); and Method (b) of is that of Bridges et al., *Tetrahedron Letters,* 33(49), 7499 (1992). $R^{1'}$ and $R^2$ are as previously defined.

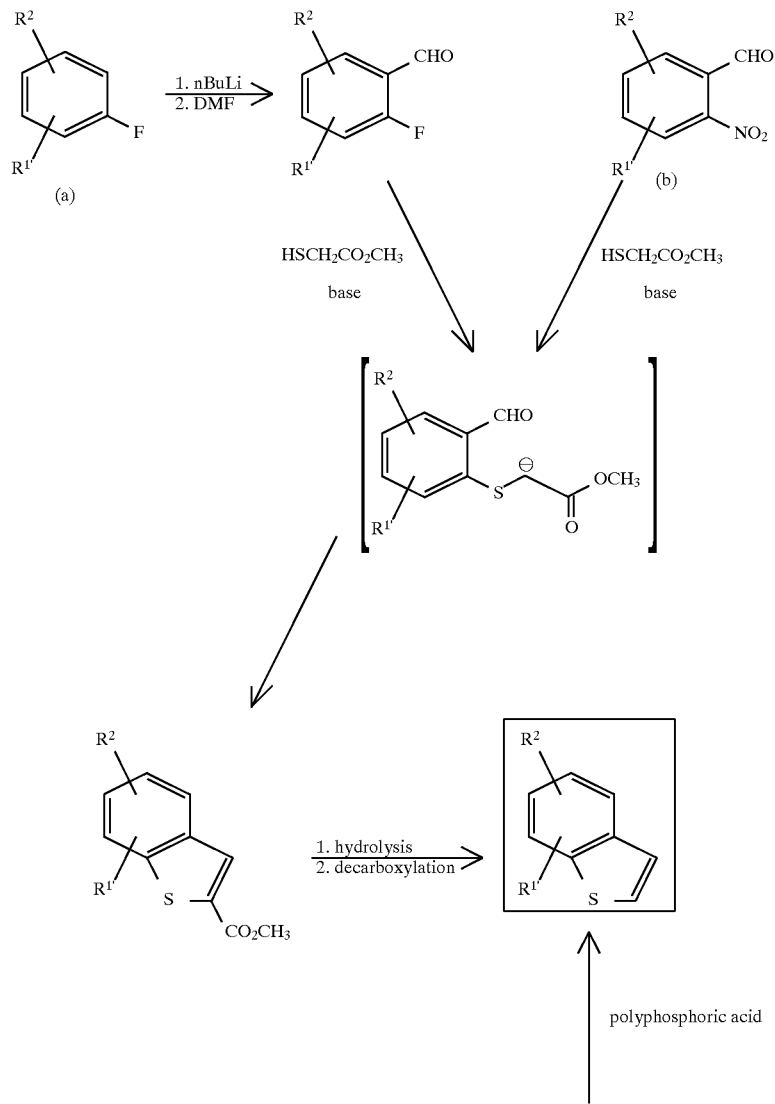

Synthetic Scheme VI

-continued
Synthetic Scheme VI

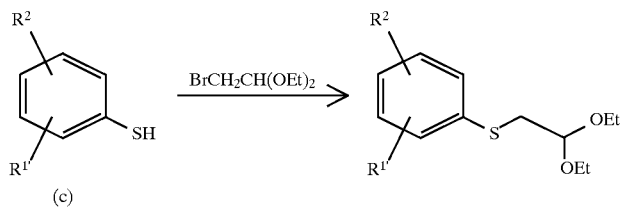

(c)

The three methods described in Synthetic Scheme VI provide the requisite benzothiophenes from three different structural classes of starting materials. The selection of a particular method is dependent upon the availability of starting materials and the stability of the substituents to the particular reaction conditions.

Method (a) of Synthetic Scheme VI takes advantage of the relative acidity of aromatic protons adjacent to a carbon bearing a fluorine atom. Treatment of an appropriate fluorobenzene with a suitable base followed by addition of dimethylformamide provides, after an aqueous acid workup, the corresponding fluorobenzaldehyde. Suitable bases for this transformation include alkyllithiums such as n-butyllithium or sec-butyllithium, and lithium amides such as lithium 2,2,6,6-tetramethylpiperidide or lithium diisopropylamide. The resulting fluorobenzaldehyde is treated with the anion of methyl thioglycollate. This anion may first be formed by treatment of a solution of methyl thioglycollate in dimethylsulfoxide with a metal hydride, preferably sodium hydride, and then adding the fluorobenzaldehyde. The exothermic reaction provides the corresponding methyl benzothiophene-2-carboxylate. Alternatively, the fluorobenzaldehyde, methyl thioglycollate and a suitable tertiary amine, preferably triethylamine, are heated together in dimethylsulfoxide to prepare the corresponding methyl benzothiophene-2-carboxylate.

An alternate route to the same methyl benzothiophene-2-carboxylate is illustrated by method (b) of Synthetic Scheme VI. This method exploits the facility with which an aromatic nitro group can undergo nucleophilic displacement. A suitable o-nitrobenzaldehyde is treated with an equimolar amount of methyl thioglycollate and potassium carbonate in dimethylformamide.

The methyl benzothiophene-2-carboxylates prepared by either of these two methods is converted to the required benzothiophene by standard ester hydrolysis/decarboxylation steps. A solution of the appropriate ester in a lower alkanol, typically methanol or ethanol, is treated with a small excess of sodium or potassium hydroxide. Once the hydrolysis is complete, volatiles are removed under reduced pressure. The residue is taken up in quinoline and to this mixture is added elemental copper. The reaction mixture is then heated to about 200° C. until the decarboxylation is complete. The desired product is isolated by normal extractive techniques and may be purified by chromatography or crystallization as appropriate prior to subsequent use.

Method (c) provides the requisite benzothiophenes from appropriately substituted thiophenols, including aminothiophenols. A solution of the thiophenol in an appropriate solvent, such as acetone, tetrahydrofuran or diethyl ether, is treated with potassium carbonate followed by bromoacetaldehyde diethyl acetal. The resulting mixture is stirred at about ambient temperature for from 1 hour to about 48 hours until the reaction is complete. The reaction mixture is then filtered and the filtrate concentrated under reduced pressure. The residue is subjected to an extractive workup and the product may be used directly in the subsequent step or purified by chromatography or crystallization if desired. This material is then dissolved in an appropriate solvent, typically a halobenzene such as chlorobenzene, and is treated with polyphosphoric acid. The reaction is heated to reflux until the cyclization is complete. The desired benzothiophene may be isolated by normal extractive workups. In those cases where $R^1$ and $R^2$ are such that isomeric benzothiophenes may result from the cyclization, the isomers may be separated by chromatographic or crystallization techniques at this or any subsequent convenient point in the synthetic pathway to compounds useful for the method of the present invention.

Those compounds useful for the method of the present invention where $R^1$ is hydroxy are easily prepared by trimethylsilyl iodide cleavage of the corresponding alkoxy compound, or catalytic O-debenzylation of the corresponding benzyloxy compound. Furthermore, compounds of this invention where $R^3$ is hydrogen may be prepared from the corresponding N-benzylated compound. Either of these hydrogenolyses may be performed by dissolution of an appropriate substrate in a lower alkanol, such as methanol or ethanol, tetrahydrofuran or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. Compounds prepared in this manner are isolated by removal of the catalyst by filtration followed by concentration of the reaction solvent under reduced pressure. The product recovered may be purified by chromatography or recrystallization from a suitable solvent if necessary.

It is evident to the skilled artisan that the conditions for hydrogenolysis of an O- or N-benzyl group are identical to those required for the hydrogenation of the 4,5-double bond of the tetrahydropyridines described supra. The hydrogenolysis and double-bond reduction steps, therefore, may be combined if desired.

The skilled artisan will appreciate that those compounds where $R^3$ is hydrogen are not only useful for the method of the present invention, but are also suitable substrates for the preparation of other useful compounds by standard synthetic techniques. The secondary amine may be alkylated with an appropriate alkylating agent, treated with an appropriate aldehyde under standard reductive alkylation conditions, or first acylated and then the resulting amide reduced to provide other compounds useful for the method of the present invention. To prepare those compounds where $R^3$ is $C_1$–$C_4$ alkyl by these techniques, the necessary reagents are readily available. To prepare those compounds where $R^3$ is ($C_1$–$C_3$ alkylene)-aryl and aryl is pyrazolyl, necessary reagents which are not commercially available may be prepared by the method described in Synthetic Scheme VII.

Synthetic Scheme VII

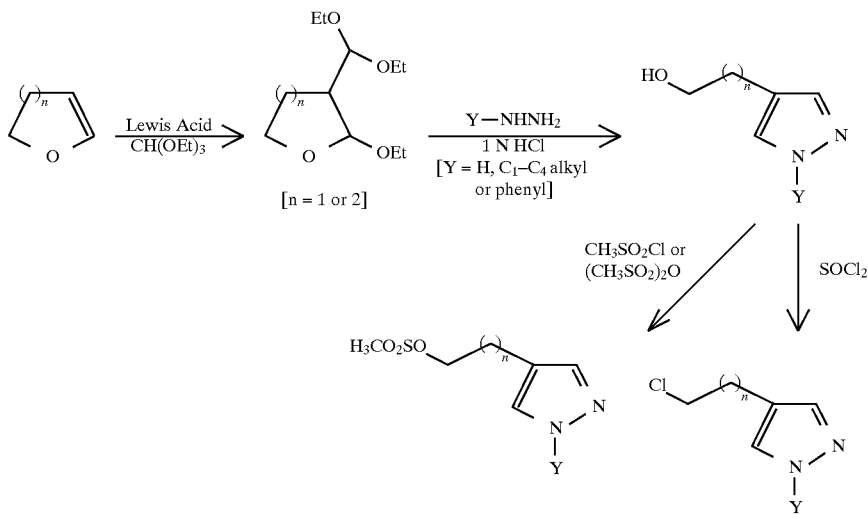

[n = 1 or 2]

[Y = H, C₁–C₄ alkyl or phenyl]

4,5-Dihydrofuran or 3,4-dihydro-2H-pyran is treated with triethylorthoformate in the presence of a Lewis acid, preferably boron trifluoride diethyl etherate, for from 1 to 4 days at ambient temperature. After treating the reaction mixture with an anhydrous base such as potassium carbonate the intermediate diacetal is distilled from the reaction mixture. This diacetal is now treated with an appropriate hydrazine, typically commercially available or synthesized by standard techniques, in aqueous acid at reflux for 4–24 hours. The product is recovered by treatment of the reaction mixture with base and extraction of the base into methylene chloride. The alcohol so recovered is suitable for treatment with thionyl chloride, methanesulfonyl chloride or methanesulfonic anhydride without further purification to provide the requisite alkylating reagents.

The following preparations and examples further illustrate the synthesis of the compounds of this invention and are not intended to limit the scope of the invention in any way. The compounds described below were identified by various standard analytical techniques as stated in the individual preparations and examples.

Preparation I 1-tert-butoxycarbonyl-4-piperidone

A solution of 9.0 gm (61.5 mmol) 4-piperidone hydrochloride monohydrate in dioxane/water at 0° C. was treated sequentially with aqueous sodium carbonate and 14.4 gm (68 mmol) 2,2-dimethylpropanoic anhydride (BOC anhydride). The resultant slurry was stirred vigorously at room temperature for 18 hours. The reaction mixture was then concentrated under reduced pressure and the residue diluted with ethyl acetate. This mixture was treated with 1.5M aqueous sodium hydrogen sulfate until the pH was about 2. The layers were separated and the remaining organics were washed with saturated aqueous sodium chloride, dried over sodium sulfate and concentrated under reduced pressure to give 9.8 gm (80%) of the title compound as a tan solid.

EA: Calculated for: $C_{10}H_{17}NO_3$: Theory: C, 60.28; H, 8.60; N, 7.03. Found: C, 60.12; H, 8.54; N, 7.11.

MS(m/e): 199(M⁺)

Preparation II 5-cyano-3-(1-benzyl-1,2,3,6-tetrahydropyridin-4-yl)-1H-indole To a solution of 5.02 gm (89.0 mMol) potassium hydroxide in 50 mL methanol were added 5.00 gm (35.17 mmol) 5-cyano-1H-indole and 7.8 mL (42.08 mmol) 1-benzyl-4-piperidone. The reaction mixture was stirred for 16 hours at reflux and then was allowed to cool. The reaction mixture was then concentrated under reduced pressure. The resultant residue was subjected to flash chromatography, eluting with dichloromethane containing 5% methanol. Fractions shown to contain product were combined and concentrated under reduced pressure to give 11.0 gm of the title compound of sufficient purity to be used in subsequent reactions.

Preparation III 3-bromo-5-chlorobenzothiophene

To a solution of 0.30 gm (1.77 mMol) 5-chlorobenzothiophene 1.0 mL acetic acid was added a solution of 0.31 gm (1.95 mMol) bromine in 1.0 mL acetic acid under a nitrogen atmosphere. The reaction was heated to 50° C. for 4 hours at which time the volatiles were removed under reduced pressure. The residue was partitioned between dichloromethane and aqueous sodium bicarbonate. The phases were separated and the organics were washed with saturated aqueous sodium chloride, dried over sodium sulfate and concentrated under reduced pressure to give 0.335 gm (76%) of the title compound as a tan solid.

m.p.=85°–860° C.

MS(FD): m/e=249 (M+2)

EA: Calculated for: $C_8H_4BrClS$: Theory: C, 38.82; H, 1.63. Found: C, 39.12; H, 1.72.

Preparation IV

1:1 mixture of 4-chloro-:6-chlorobenzothiophene 2-(3-chlorophenylthio)acetaldehyde diethyl acetal To a stirring mixture of 20.0 gm (0.138 mol) 3-chlorothiophenol and 21.0 gm (0.15 mol) potassium carbonate in 220 mL acetone were added dropwise 1.1 equivalents of bromoacetaldehyde diethyl acetal. After stirring for 17 hours at ambient temperature, the reaction mixture was filtered and the filtrate concentrated under reduced pressure. The resulting residue was partitioned between diethyl ether and water. The organic phase was separated, washed with saturated sodium chloride, dried over sodium sulfate and concentrated under reduced pressure to give 35.1 gm (97%) of the desired. compound as a rust colored oil.

MS(FD): m/e=260 (M$^+$)

EA: Calculated for: $C_{12}H_{17}O_2ClS$: Theory: C, 55.27; H. 6.57. Found: C, 55.37; H, 6.35.

Cyclization

To a mixture of 12.8 gm polyphosphoric acid in 100 mL refluxing chlorobenzene were added dropwise a solution of 6.0 gm (0.023 mol) 2-(3-chlorophenylthio)acetaldehyde diethyl acetal in 20 mL chlorobenzene. The resulting slurry was stirred at reflux for 1 hour and was then cooled to ambient temperature. The organics were decanted, washed with saturated aqueous sodium chloride, dried over sodium sulfate and concentrated under reduced pressure to give 2.75 gm (71%) of the title mixture as a rust-colored oil. This material was suitable for subsequent steps without further purification.

Preparation V 2-(1-methyl-1H-pyrazol-3-yl)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M$^+$)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126(M$^+$)

$^1$H-NMR(DMSO-d$_6$): δ7.45 (s, 1H); 7.25 (s, 1H); 4.65 (t, 1H); 3.75 (s,3H); 3.55 (m, 2H); 2.55 (t, 2H).

Preparation VI 2-(1-isopropyl-1H-pyrazol-3-yl)-1-ethanol

To a solution of 1.0 gm (9.0 mmol) 2-(3-pyrazolyl)-1-ethanol in 36 mL dimethylformamide were added 2.38 gm (22.5 mmol) sodium carbonate followed by the dropwise addition of a solution of 0.89 mL (9.0 mMol) 2-iodopropane in 8 mL dimethylformamide. The reaction mixture was heated to 100° C. for 18 hours. The reaction mixture was then cooled to ambient and then concentrated under reduced pressure. The residue was partitioned between water and dichloromethane. The organic phase was then washed with water followed by saturated aqueous sodium chloride and was then dried over sodium sulfate. The remaining organics were concentrated under reduced pressure to give 0.36 gm (26.0%) of the title compound as a brown oil.

$^1$H-NMR(DMSO-d$_6$): δ7.50 (s, 1H); 7.25 (s, 1H); 4.60 (t, 1H); 4.40 (m, 1H); 3.50 (m, 2H); 2.55 (t, 2H); 1.35(d, 6H).

Preparation VII 4-cyclopropylmethoxy-1H-indole

A solution of 5.00 gm (37.6 mmol) 4-hydroxyindole in dimethylformamide was added dropwise over 30 minutes to a solution of 1.65 gm (41.3 mMol) sodium hydride (60% suspension in mineral oil) in 25 mL dimethylformamide at 0° C. The resulting black solution was stirred at room temperature for 2 hours and then a solution of 3.6 mL (37.6 mMol) cyclopropylmethyl bromide in 10 mL dimethylformamide was added dropwise. The resulting mixture was stirred for 1.5 hours at room temperature. The reaction mixture was then quenched by the addition of 100 mL water and the resulting mixture extracted well with ethyl acetate. The organic phases were combined, washed sequentially with water and saturated aqueous sodium chloride, dried over sodium sulfate and concentrated under reduced pressure. The residue was subjected to silica gel chromatography, eluting with 10% ethyl acetate in hexane. Fractions shown to contain product were combined and concentrated under reduced pressure to provide 4.48 gm (64%) of the title compound as an amber oil.

Preparation VIII 1,2-dimethylpiperidin-4-one

Ethyl 3-(N-methylamino)butanoate

A solution of 479.2 mL (0.958 mole) methylamine (2M in tetrahydrofuran) was added dropwise to 99.44 gm ethyl crotonate with stirring. After stirring 5 days at room temperature the reaction mixture was concentrated under reduced pressure to remove tetrahydrofuran. The residue was distilled to provide 91.25 gm (72%) of the desired product in 2 fractions.

MS(FD): m/e=145 (M$^+$)

EA: Calculated for: $C_7H_{15}NO_2$: Theory: C, 57.90; H, 10.41; N, 9.65. Found: C, 57.61; H, 10.66; N, 9.88.

Ethyl 3-(N-methyl-N-(2-ethoxycarbonyleth-1-yl)amino)butanoate

A mixture of 54.4 gm (0.374 mole) ethyl 3-(N-methylamino)butanoate and 100 gm (0.999 mole) ethyl acrylate was heated at 110° C. with stirring for 18 hours. The reaction mixture was cooled to room temperature and then distilled under reduced pressure to provide 61.7 gm (67.1%) of the desired compound.

b.p.=93°–100° C. (0.12 mm Hg)

MS(FD): m/e=245 (M$^+$)

EA: Calculated for: $C_{12}H_{23}NO_4$: Theory: C, 58.75; H. 9.45; N, 5.71. Found: C, 59.02; H, 9.65; N, 6.00.

Cyclization/decarboxylation

A solution of 43.0 gm (0.175 mole) ethyl 3-(N-methyl-N-(2-ethoxycarbonyleth-1-yl)amino)butanoate in 150 mL benzene was added dropwise to a stirring suspension of 5.6 gm (0.14 mole) sodium hydride (60% dispersion in mineral oil) in 100 mL benzene at room temperature. To this gelatinous mixture were added an additional 250 mL benzene and 3.5 gm (0.088 mole) sodium hydride (60% dispersion in mineral oil) and the mixture heated to reflux for 2 hours. The reaction mixture was then cooled to room temperature and acidified by the addition of concentrated hydrochloric acid. The phases were separated and the organic phase extracted with 3×100 mL 5N hydrochloric acid. The combined aqueous phases were allowed to stand at room temperature for 18 hours and were then heated to reflux for 4 hours. The reaction mixture was cooled to 0° C. and basified (pH~14) with 50% aqueous NaOH. The mixture was extracted with 4×200 mL dichloromethane. The combined organic extracts were dried over sodium sulfate and then concentrated under reduced pressure to provide 22.2 gm of a brown oil. This residual oil was subjected to silica gel chromatography, eluting with 5% methanol in dichloromethane containing a trace of ammonium hydroxide. Fractions shown to contain product were combined and concentrated under reduced pressure to provide 18.7 gm of an oil. This oil was fractionally distilled to provide 10.2 gm (46%) of the title compound.

MS(FD): m/e=127 (M$^+$)

EA: Calculated for: C$_7$H$_{13}$NO: Theory: C, 66.10; H, 10.30; N, 11.01. Found: C, 65.80; H, 10.44; N, 11.04.

Preparation IX 3-bromo-6-chlorobenzothiophene

A solution of 1.41 gm (8.9 mMol) bromine in 5 mL acetic acid was added dropwise to a solution of 3.0 gm (17.8 mMol) of a 1:1 mixture of 4- and 6-chlorobenzothiophene (Preparation IV) in 10 mL acetic acid. The reaction mixture was stirred at 50° C. for about 4 hours. The reaction mixture was then concentrated under reduced pressure and the residue dissolved in dichloromethane. The organic solution was then washed sequentially with saturated aqueous sodium bicarbonate and saturated aqueous sodium chloride. The remaining organics were dried over sodium sulfate and concentrated under reduced pressure to provide a red oil which crystallized upon standing. This residue was recrystallized from pentane to provide 0.78 gm (35%) of the title compound as a colorless solid.

MS(FD): m/e=246 (M$^+$)

EA: Calculated for: C$_8$H$_4$ClBrS: Theory: C, 38.82; H. 1.63. Found: C, 39.05; H, 1.72.

EXAMPLE 1

4-fluoro-3-(1-methyl-1,2,3,6-tetrahydropyridin-4-yl)-1H-indole

To a solution of 1.18 gm (21.0 mMol) potassium hydroxide in 10 mL methanol were added 1.00 gm (7.4 mMol) 4-fluoro-1H-indole and 1.82 mL (14.8 mMol) 1-methyl-4-piperidone. The reaction mixture was stirred at reflux for 28 hours and then was allowed to cool. The crystals which formed were filtered, washed with methanol and dried under vacuum at 60° C. to give 1.17 gm (69%) of the title compound.

m.p.=213°–216° C.

MS(FD): m/e=230 (M$^+$)

EA: Calculated for: C$_{14}$H$_{15}$N$_2$F: Theory: C, 73.02; H, 6.57; N, 12.17. Found: C, 73.07; H, 6.65; N, 12.40.

The compounds of Examples 2–14 were prepared by the procedure described in detail in Example 1.

EXAMPLE 2

5-fluoro-3-(1-methyl-1,2,3,6-tetrahydropyridin-4-yl)-1H-indole

Beginning with 1.00 gm (7.4 mMol) 5-fluoro-1H-indole and 1.82 mL (14.8 mmol) 1-methyl-4-piperidone, 1.60 gm (94%) of the title compound were recovered as a crystalline solid.

m.p.=231°–233° C.

MS(FD): m/e=230 (M$^+$)

EA: Calculated for: C$_{14}$H$_{15}$N$_2$F: Theory: C, 73.02; H, 6.57; N, 12.17. Found: C, 72.98; H. 6.56; N, 11.97.

EXAMPLE 3

6-fluoro-3-(1-methyl-1,2,3,6-tetrahydropyridin-4-yl)-1H-indole

Beginning with 1.00 gm (7.4 mMol) 6-fluoro-1H-indole and 1.82 mL (14.8 mMol) 1-methyl-4-piperidone, 1.18 gm (70%) of the title compound were recovered as a colorless crystalline solid.

m.p.=245°–247° C.

MS(FD): m/e=230 (M$^+$)

EA: Calculated for: C$_{14}$H$_{15}$N$_2$F: Theory: C, 73.02; H, 6.57; N, 12.17. Found: C, 73.32; H, 6.66; N, 12.20.

EXAMPLE 4

7-fluoro-3-(1-methyl-1,2,3,6-tetrahydropyridin-4-yl)-1H-indole

Beginning with 0.50 gm (3.70 mMol) 7-fluoro-1H-indole and 0.91 mL (7.4 mMol) 1-methyl-4-piperidone, 0.64 gm (75%) of the title compound were recovered as a white solid.

m.p.=245°–247° C.

MS(FD): m/e=230 (M$^+$)

EA: Calculated for: C$_{14}$H$_{15}$N$_2$F: Theory: C, 73.02; H, 6.57; N, 12.17. Found: C, 73.30; H, 6.68; N, 12.32.

EXAMPLE 5

6-chloro-3-(1-methyl-1,2,3,6-tetrahydropyridin-4-yl)-1H-indole

Beginning with 1.00 gm (6.6 mMol) 6-chloro-1H-indole and 1.6 mL (13.0 mMol) 1-methyl-4-piperidone, 1.7 gm (100%) of the title compound were recovered as a pale yellow solid.

m.p.=245°–247° C.

MS(FD): m/e=246 (M–1)

EA: Calculated for: C$_{14}$H$_{15}$N$_2$Cl: Theory: C, 68.15; H, 6.13; N, 11.35. Found: C, 68.12; H, 6.22; N, 11.36.

EXAMPLE 6

7-chloro-3-(1-methyl-1,2,3,6-tetrahydropyridin-4-yl)-1H-indole

Beginning with 0.50 gm (3.3 mMol) 7-chloro-1H-indole and 0.81 mL (6.6 mMol) 1-methyl-4-piperidone, 0.66 gm (81%) of the title compound were recovered as a white solid.

m.p.=242°–244° C.

MS(FD): m/e=246 (M–1)

EA: Calculated for: C$_{14}$H$_{15}$N$_2$Cl: Theory: C, 68.15; H, 6.13; N, 11.36. Found: C, 67.97; H, 6.16; N, 11.59.

EXAMPLE 7

6-trifluoromethyl-3-(1-methyl-1,2,3,6-tetrahydropyridin-4-yl)-1H-indole

Beginning with 1.00 gm (5.4 mMol) 6-trifluoromethyl-1H-indole and 1.33 mL (11.0 mMol) 1-methyl-4-piperidone, 1.34 gm (89%) of the title compound were recovered as colorless crystals.

m.p.=279°–280° C. (dec.)

MS(FD): m/e=280 (M⁺)

EA: Calculated for: $C_{15}H_{15}N_2F_3$: Theory: C, 64.28; H, 5.39; N, 9.99. Found: C, 64.52; H, 5.16; N, 10.07.

EXAMPLE 8

6-nitro-3-(1-methyl-1,2,3,6-tetrahydropyridin-4-yl)-1H-indole

Beginning with 2.00 gm (12.3 mMol) 6-nitro-1H-indole and 3.00 mL (24.7 mMol) 1-methyl-4-piperidone, 2.57 gm (81%) of the title compound were recovered as a yellow solid.

MS(FD): m/e=257 (M⁺)

EA: Calculated for: $C_{14}H_{15}N_3O_2$: Theory: C, 65.36; H, 5.88; N, 16.33. Found: C, 65.33; H, 5.89; N, 16.29.

EXAMPLE 9

5,6-dichloro-3-(1-methyl-1,2,3,6-tetrahydropyridin-4-yl)-1H-indole

Beginning with 0.136 gm (0.88 mMol) 5,6-dichloro-1H-indole and 0.216 mL (1.75 mMol) 1-methyl-4-piperidone, 0.150 gm (61%) of the title compound were recovered as a white solid.

m.p.=255°–257° C.

MS(FD): m/e=280 (M−1)

EA: Calculated for: $C_{14}H_{14}N_2Cl_2$: Theory: C, 59.80; H, 5.02; N, 9.96. Found: C, 59.65; H, 4.85; N, 9.91.

EXAMPLE 10

6,7-dichloro-3-(1-methyl-1,2,3,6-tetrahydropyridin-4-yl)-1H-indole

Beginning with 0.50 gm (2.7 mMol) 6,7-dichloro-1H-indole and 0.66 mL (5.4 mMol) 1-methyl-4-piperidone, 0.72 gm (95%) of the title compound were recovered as a white solid.

m.p.=246°–249° C.

MS(FD): m/e=280 (M−1)

EA: Calculated for: $C_{14}H_{14}N_2Cl_2$: Theory: C, 59.80; H, 5.02; N, 9.96. Found: C, 60.04; H, 5.04; N, 10.21.

EXAMPLE 11

5-(thien-2-yl)methyloxy-3-(1-methyl-1,2,3,6-tetrahydropyridin-4-yl)-1H-indole

Beginning with 0.60 gm (2.7 mMol) 5-(thien-2-yl)methyl-oxy-1H-indole and 0.64 mL (5.2 mMol) 1-methyl-4-piperidone, 0.11 gm (13%) of the title compound were recovered as a solid.

m.p.=197°–199° C.

MS(FD): m/e=324 (M⁺)

EA: Calculated for: $C_{19}H_{20}N_2OS$: Theory: C, 70.34; H, 6.21; N, 8.63. Found: C, 70.28; H, 6.16; N, 8.40.

EXAMPLE 12

4-cyclopropylmethyloxy-3-(1-methyl-1,2,3,6-tetrahydropyridin-4-yl)-1H-indole

Beginning with 4.3 gm (22.9 mMol) 4-cyclopropylmethyloxy-1H-indole and 5.7 mL (45.9 mMol) 1-methyl-4-piperidone, 0.995 gm (33% based on recovered starting material) of the title compound were recovered as a light yellow solid.

MS(FD): m/e=282 (M⁺)

EA: Calculated for: $C_{18}H_{22}N_2O$: Theory: C, 76.56; H, 7.85; N, 9.92. Found: C, 76.30; H, 7.71; N, 9.78.

EXAMPLE 13

4-cyclopropylmethyloxy-3-(1-benzyl-1,2,3,6-tetrahydropyridin-4-yl)-1H-indole

Beginning with 3.77 gm (20.1 mMol) 4-cyclopropylmethyl-oxy-1H-indole and 7.5 mL (40.3 nMol) 1-benzyl-4-piperidone, 1.68 gm (23%) of the title compound were recovered as an off white solid.

MS(FD): m/e=358 (M⁺)

EA: Calculated for: $C_{24}H_{26}N_2O$: Theory: C, 80.41; H, 7.31; N, 7.81. Found: C, 80.70; H, 7.21; N, 7.96.

EXAMPLE 14

6-chloro-3-(1,3-dimethyl-1,2,3,6-tetrahydropyridin-4-yl)-1H-indole

Beginning with 0.97 gm (6.4 mMol) 6-chloro-1H-indole and 1.6 gm (13.0 mMol) 1,3-dimethyl-4-piperidone, 1.05 gm (63%) of the title compound were recovered as a crystalline solid.

m.p.=170°–172° C.

MS(FD): m/e=260 (M⁺)

EA: Calculated for: $C_{15}H_{17}N_2Cl$: Theory: C, 69.09; H, 6.57; N, 10.74. Found: C, 69.39; H, 6.40; N, 10.97.

EXAMPLE 15

5-cyano-3-(1,2,5,6-tetrahydropyridin-4-yl)-1H-indole

To a solution of 8.8 gm (157 mMol) potassium hydroxide in 85 mL methanol were added 8.15 gm (57.33 mMol) 5-cyano-1H-indole and 7.86 gm (51.17 mMol) 4-piperidone hydrochloride monohydrate. The resulting mixture was heated to reflux for 48 hours and was then allowed to cool to room temperature. The reaction mixture was concentrated under reduced pressure to about half volume and was then treated with 1M HCl until the pH of the solution was between 1 and 2. The resulting solution was extracted twice with 100 mL of diethyl ether and the remaining aqueous phase was treated with 5N sodium hydroxide until the pH of the solution was between 12 and 14. This aqueous phase was extracted 5 times with 10% methanol in dichloromethane. These organic phases were combined, dried over sodium sulfate and concentrated under reduced pressure to a residue. This residue was subjected to flash silica gel chromatography, eluting with dichloromethane which contained 20% methanol and 2% ammonium hydroxide. Fractions shown to contain product were combined and concentrated under reduced pressure to give 6.86 gm (60%) of the title compound as a solid.

m.p.=185°–187° C.

MS(FD): m/e=223 (M⁺)

The compounds of Examples 16–31 were prepared by the procedure described in detail in Example 15.

EXAMPLE 16

5-fluoro-3-(1,2,3,6-tetrahydropyridin-4-yl)-1H-indole

Beginning with 4.0 gm (29.6 mMol) 5-fluoro-1H-indole and 9.13 gm (59.0 mMol) 4-piperidone hydrochloride monohydrate, 4.60 gm (72%) of the title compound were recovered as a white solid.

m.p.=175°–177° C.

MS(FD): m/e=216 (M$^+$)

EA: Calculated for: $C_{13}H_{13}N_2F$: Theory: C, 72.20; H, 6.06; N, 12.95. Found: C, 72.00; H, 6.15; N, 12.91.

EXAMPLE 17

6-fluoro-3-(1,2,3,6-tetrahydropyridin-4-yl)-1H-indole

Beginning with 11.6 gm (86.0 mMol) 6-fluoro-1H-indole and 26.5 gm (172 mMol) 4-piperidone hydrochloride monohydrate, 11.0 gm (59%) of the title compound were recovered as a light tan solid.

m.p.=205°–209° C.

MS(FD): m/e=216 (M$^+$)

EA: Calculated for: $C_{13}H_{13}N_2F$: Theory: C, 72.20; H, 6.06; N, 12.95. Found: C, 71.92; H, 6.31; N, 13.05.

EXAMPLE 18

7-fluoro-3-(1,2,3,6-tetrahydropyridin-4-yl)-1H-indole

Beginning with 2.0 gm (14.8 mMol) 7-fluoro-1H-indole and 4.6 gm (30.0 mMol) 4-piperidone hydrochloride monohydrate, 2.1 gm (66%) of the title compound were recovered as a white solid.

m.p.=186°–188° C.

MS(FD): m/e=216 (M$^+$)

EA: Calculated for: $C_{13}H_{13}N_2F$: Theory: C, 72.20; H, 6.06; N, 12.95. Found: C, 72.41; H, 6.24; N, 13.09.

EXAMPLE 19

5-chloro-3-(1,2,3,6-tetrahydropyridin-4-yl)-1H-indole

Beginning with 3.0 gm (20.0 mMol) 5-chloro-1H-indole and 6.0 gm (40.0 mMol) 4-piperidone hydrochloride monohydrate, 1.45 gm (31%) of the title compound were recovered as a yellow solid.

m.p.=185°–188° C.

MS(FD): m/e=234 (M$^+$)

EA: Calculated for: $C_{13}H_{13}N_2Cl$: Theory: C, 67.10; H, 5.63; N, 12.04. Found: C, 67.38; H, 5.58; N, 12.25.

EXAMPLE 20

6-chloro-3-(1,2,3,6-tetrahydropyridin-4-yl)-1H-indole

Beginning with 4.0 gm (26.0 mMol) 6-chloro-1H-indole and 8.0 gm (52.0 mMol) 4-piperidone hydrochloride monohydrate, 3.7 gm (61%) of the title compound were recovered as a yellow solid.

m.p.=181°–185° C.

MS(FD): m/e=234 (M$^+$)

EA: Calculated for: $C_{13}H_{13}N_2Cl$: Theory: C, 67.10; H, 5.63; N, 12.04. Found: C, 67.13; H, 5.70; N, 12.18.

EXAMPLE 21

7-chloro-3-(1,2,3,6-tetrahydropyridin-4-yl)-1H-indole

Beginning with 0.70 gm (4.6 mMol) 7-chloro-1H-indole and 1.4 gm (9.2 mMol) 4-piperidone hydrochloride monohydrate, 0.80 gm (75%) of the title compound were recovered as a yellow solid.

m.p.=205°–208° C.

MS(FD): m/e=234 (M$^+$)

EA: Calculated for: $C_{13}H_{13}N_2Cl$: Theory: C, 67.10; H. 5.63; N, 12.04. Found: C, 67.06; H; 5.85; N, 12.01.

EXAMPLE 22

5-bromo-3-(1,2,3,6-tetrahydropyridin-4-yl)-1H-indole

Beginning with 6.2 gm (31.6 mMol) 5-bromo-1H-indole and 4.7 gm (30.6 mMol) 4-piperidone monohydrate hydrochloride, 7.93 gm (93%) of the title compound were recovered as a solid.

m.p.=202°–204° C.

MS(FD): m/e=277.17 (M$^+$)

EXAMPLE 23

6-trifluoromethyl-3-(1,2,3,6-tetrahydropyridin-4-yl)-1H-indole

Beginning with 4.0 gm (22.0 mMol) 6-trifluoromethyl-1H-indole and 6.6 gm (43.0 mMol) 4-piperidone hydrochloride monohydrate, 3.7 gm (64%) of the title compound were recovered as a white solid.

MS(FD): m/e=266 (M$^+$)

EA: Calculated for: $C_{14}H_{13}N_2F_3$: Theory: C, 63.15; H, 4.92; N, 10.52. Found: C, 62.90; H, 4.96; N, 10.57.

EXAMPLE 24

6-nitro-3-(1,2,3,6-tetrahydropyridin-4-yl)-1H-indole

Beginning with 6.0 gm (37.0 mMol) 6-nitro-1H-indole and 11.4 gm (74.0 mMol) 4-piperidone hydrochloride monohydrate, 8.8 gm (97%) of the title compound were recovered as an orange solid.

m.p.=247°–250° C. (dec.)

MS(FD): m/e=243 (M$^+$)

EA: Calculated for: $C_{13}H_{13}N_3O_2$: Theory: C, 64.19; H, 5.39; N, 17.27. Found: C, 64.37; H, 5.40; N, 17.50.

EXAMPLE 25

5-methoxy-3-(1,2,3,6-tetrahydropyridin-4-yl)-1H-indole

Beginning with 5.0 gm (34.0 mMol) 5-methoxy-1H-indole and 10.0 gm (65.0 mMol) 4-piperidone hydrochloride monohydrate, 6.1 gm (79%) of the title compound were recovered as a yellow solid.

m.p.=191°–195° C.

MS(FD): m/e=228 (M$^+$)

EA: Calculated for: $C_{14}H_{16}N_2O$: Theory: C, 73.66; H, 7.06; N, 12.27. Found: C, 73.38; H, 7.08; N, 12.36.

EXAMPLE 26

6-methoxy-3-(1,2,3,6-tetrahydropyridin-4-yl)-1H-indole

Beginning with 2.0 gm (14.0 mMol) 6-methoxy-1H-indole and 4.2 gm (27.0 mMol) 4-piperidone hydrochloride monohydrate, 2.8 gm (90%) of the title compound were recovered as a yellow solid.

m.p.=190°–193° C.

MS(FD): m/e=228 (M$^+$)

EA: Calculated for: $C_{14}H_{16}N_2O$: Theory: C, 73.66; H, 7.06; N, 12.27. Found: C, 73.44; H, 7.16; N, 12.37.

EXAMPLE 27

6,7-dichloro-3-(1,2,3,6-tetrahydropyridin-4-yl)-1H-indole

Beginning with 1.4 gm (7.5 mMol) 6,7-dichloro-1H-indole and 2.3 gm (15.0 mMol) 4-piperidone hydrochloride monohydrate, 1.8 gm (89%) of the title compound were recovered as a white solid.

m.p.=252°–254° C.

MS(FD): m/e=268 (M$^+$)

EA: Calculated for: $C_{13}H_{12}N_2Cl_2$: Theory: C, 58.45; H, 4.53; N, 10.49. Found: C, 58.71; H, 4.64; N, 10.33.

EXAMPLE 28

5-methoxy-6-chloro-3-(1,2,3,6-tetrahydropyridin-4-yl)-1H-indole

Beginning with 2.0 gm (11.0 mMol) 5-methoxy-6-chloro-1H-indole and 3.4 gm (22.0 mMol) 4-piperidone hydrochloride monohydrate, 2.4 gm (83%) of the title compound were recovered as a yellow solid.

m.p.=222°–224° C.

MS(FD): m/e=264 (M$^+$)

EA: Calculated for: $C_{14}H_{15}N_2OCl$: Theory: C, 64.00; H, 5.75; N, 10.66. Found: C, 64.12; H, 5.86; N, 10.57.

EXAMPLE 29

7-cyclopropyl-3-(1,2,3,6-tetrahydropyridin-4-yl)-1H-indole

Beginning with 2.0 gm (12.7 mMol) 7-cyclopropyl-1H-indole and 3.9 gm (25.0 mMol) 4-piperidone hydrochloride monohydrate, 1.66 gm (55%) of the title compound were recovered as a white solid.

m.p.=186°–189° C.

MS(FD): m/e=238 (M$^+$)

EA: Calculated for: $C_{16}H_{18}N_2$: Theory: C, 80.63; H, 7.61; N, 11.75. Found: C, 80.39; H, 7.81; N, 11.79.

EXAMPLE 30

6-methyl-3-(1,2,3,6-tetrahydropyridin-4-yl)-1H-indole

Beginning with 3.0 gm (28.0 mMol) 6-methyl-1H-indole and 7.04 gm (45.7 mMol) 4-piperidone hydrochloride monohydrate, 1.1 gm (22%) of the title compound were recovered as a tan powder.

EA: Calculated for: $C_{16}H_{16}N_2$: Theory: C, 79.21; H, 7.60; N, 13.20. Found: C, 78.94; H, 7.67; N, 12.93.

EXAMPLE 31

7-methyl-3-(1,2,3,6-tetrahydropyridin-4-yl)-1H-indole

Beginning with 2.0 gm (15.0 mMol) 6-methyl-1H-indole and 4.69 gm (30.0 mMol) 4-piperidone hydrochloride monohydrate, 2.2 gm (68%) of the title compound were recovered as a yellow solid.

HRMS: Calculated for: $C_{16}H_{16}N_2$: Theory: m/e=213.139174. Found: m/e=213.141200.

Standard Procedure for the Hydrogenation of 3-(1,2,3,6-tetrahydropyridin-4-yl)-1H-indoles The 3-(1,2,3,6-tetrahydropyridin-4-yl)-1H-indole (10.0 mMol) is dissolved in a lower alkanol such as ethanol (100 mL). A precious metal catalyst, for example platinum(IV) oxide, (0.5 g) is added and the mixture shaken under 40 to 60 psi of hydrogen at ambient temperature to 40° C. for 16 h to 3 days. The resulting mixture is filtered through Celite and the filter cake washed with the lower alkanol solvent. The filtrate is concentrated under reduced pressure to typically yield a solid. The 3-(piperidin-4-yl)-1H-indole can be used without further purification or can be recrystallized, subjected to chromatography or a salt formed as appropriate.

The compounds of Examples 32–42 were prepared by the Standard Procedure described in the preceding paragraph.

EXAMPLE 32

6-fluoro-3-(1-methylpiperidin-4-yl)-1H-indole hydrochloride

Beginning with 5.3 gm (20.0 mMol) 6-fluoro-3-(1-methyl-1,2,3,6-tetrahydropyridin-4-yl)-1H-indole, 2.8 gm (52%) of the title compound were recovered as a crystalline solid from acetonitrile.

m.p.=187°–189° C.

MS(FD): m/e=232 (M$^+$)

EA: Calculated for: $C_{14}H_{17}N_2F.HCl$: Theory: C, 62.57; H, 6.75; N, 10.42. Found: C, 62.34; H, 6.76; N, 10.57.

EXAMPLE 33

6-chloro-3-(1-methylpiperidin-4-yl)-1H-indole hydrochloride

Beginning with 1.6 gm (6.5 mMol) 6-chloro-3-(1-methyl-1,2,3,6-tetrahydropyridin-4-yl)-1H-indole, 1.4 gm (76%) of the title compound were recovered as a white solid from acetonitrile.

m.p.=234°–236° C.

MS(FD): m/e=248 (M$^+$)

EA: Calculated for: $C_{14}H_{17}N_2Cl.HCl$: Theory: C, 58.96; H, 6.36; N, 9.82. Found: C, 58.73; H, 6.16; N, 10.01.

EXAMPLE 34

7-chloro-3-(1-methylpiperidin-4-yl)-1H-indole hydrochloride

Beginning with 3.0 gm (12.1 mMol) 7-chloro-3-(1-methyl-1,2,3,6-tetrahydropyridin-4-yl)-1H-indole, 2.8 gm (81%) of the title compound were recovered as a solid from acetonitrile.

m.p.=206°–208° C.

MS(FD): m/e=248 (M$^+$)

EA: Calculated for: $C_{14}H_{17}N_2Cl.HCl$: Theory: C, 58.96; H, 6.36; N, 9.82. Found: C, 58.71; H, 6.29; N, 9.76.

EXAMPLE 35

6-fluoro-3-(piperidin-4-yl)-1H-indole

Beginning with 19.2 gm (89.0 mMol) 6-fluoro-3-(1,2,3,6-tetrahydropyridin-4-yl)-1H-indole, 18.5 gm (96%) of the title compound were recovered as a white solid.

m.p.=234°–236° C.

MS(FD): m/e=218 (M$^+$)

EA: Calculated for: $C_{13}H_{15}N_2F$: Theory: C, 71.53; H, 6.93; N, 12.83. Found: C, 71.77; H, 7.11; N, 13.00.

EXAMPLE 36

6-chloro-3-(piperidin-4-yl)-1H-indole hydrochloride

Beginning with 1.0 gm (4.3 mMol) 6-chloro-3-(1,2,3,6-tetrahydropyridin-4-yl)-1H-indole, 0.65 gm (56%) of the title compound were recovered as a white solid.

m.p.=290°–294° C. (dec.)

MS(FD): m/e=234 (M$^+$)

EA: Calculated for: $C_{13}H_{15}N_2Cl.HCl$: Theory: C, 57.58; H, 5.95; N, 10.33. Found: C, 57.30; H, 6.15; N, 10.57.

EXAMPLE 37

7-chloro-3-(piperidin-4-yl)-1H-indole hydrochloride

Beginning with 1.2 gm (5.2 mMol) 7-chloro-3-(1,2,3,6-tetrahydropyridin-4-yl)-1H-indole, 0.77 gm (55%) of the title compound were recovered as a light brown solid from n-propanol.

m.p.=294°–297° C. (dec.)

MS(FD): m/e=234 (M$^+$)

EA: Calculated for: $C_{13}H_{15}N_2Cl.HCl$: Theory: C, 57.58; H, 5.95; N, 10.33. Found: C, 57.39; H, 6.04; N, 10.11.

EXAMPLE 38

6-trifluoromethyl-3-(piperidin-4-yl)-1H-indole

Beginning with 2.1 gm (7.9 mMol) 6-trifluoromethyl-3-(1,2,3,6-tetrahydropyridin-4-yl)-1H-indole, 1.2 gm (57%) of the title compound were recovered as a yellow solid.

m.p.=210°–214° C.

MS(FD): m/e=268 (M$^+$)

EXAMPLE 39

6,7-dichloro-3-(piperidin-4-yl)-1H-indole

Beginning with 4.5 gm (16.8 mMol) 6,7-di-chloro-3-(1,2,3,6-tetrahydropyridin-4-yl)-1H-indole, 4.1 gm (91%) of the title compound were recovered as a white solid.

m.p.=254°–257° C.

MS(FD): m/e=270 (M$^+$)

EA: Calculated for: $C_{13}H_{14}N_2Cl_2$: Theory: C, 58.01; H, 5.24; N, 10.41. Found: C, 58.25; H, 5.42; N, 10.64.

EXAMPLE 40

5-cyano-3-(piperidin-4-yl)-1H-indole

A mixture of 0.92 gm (2.9 mMol) 5-cyano-3-(1-benzyl-1,2,3,6-tetrahydropyridin-4-yl)-1H-indole, 1.85 gm (29.3 mMol) ammonium formate and 0.26 gm 5% palladium on carbon in 40 mL methanol were stirred at reflux for 45 minutes. The reaction mixture was then filtered through a pad of Celite and the filtrate concentrated under reduced pressure. The residue was subjected to flash silica gel chromatography, eluting with dichloromethane containing 20% methanol and 2% ammonium hydroxide. Fractions shown to contain product were combined and concentrated under reduced pressure to give 0.36 gm (55%) of the title compound.

m.p.=201°–203° C.

MS(FD): m/e=225 (M$^+$)

EXAMPLE 41

6-methyl-3-(piperidin-4-yl)-1H-indole

Beginning with 0.3 gm (1.4 mMol) 6-methyl-3-(1,2,3,6-tetrahydropyridin-4-yl)-1H-indole, 0.22 gm (73%) of the title compound were recovered as a tan solid.

HRMS: Calculated for: $C_{16}H_{18}N_2$: Theory: m/e=215.154824. Found: m/e=215.156400.

EXAMPLE 42

7-methyl-3-(piperidin-4-yl)-1H-indole

Beginning with 0.3 gm (1.4 mMol) 7-methyl-3-(1,2,3,6-tetrahydropyridin-4-yl)-1H-indole, 0.29 gm (96%) of the title compound were recovered as a tan solid.

HRMS: Calculated for: $C_{16}H_{18}N_2$: Theory: m/e=215.154824. Found: m/e=215.156200.

EXAMPLE 43

6-nitro-3-(piperidin-4-yl)-1H-indole trifluoroacetate

To a mixture of 2.4 gm (9.9 mMol) 6-nitro-3-(1,2,3,6-tetrahydropyridin-4-yl)-1H-indole in 10.0 mL trifluoroacetic acid were added 1.65 mL (10.4 mMol) triethylsilane. After an initial exotherm, the reaction was allowed to stir for 18 hours at ambient temperature. At this point an additional 0.5 mL triethylsilane were added and the reaction mixture stirred for 24 hours. The reaction mixture was then concentrated under reduced pressure. The residue was crystallized from ethanol to give 2.4 gm (67%) of the title compound.

m.p.=212°–214° C.

MS(FD): m/e=245 (M$^+$)

EA: Calculated for: $C_{13}H_{15}N_2O_2.CF_3CO_2H$: Theory: C, 50.14; H, 4.48; N, 11.69. Found: C, 50.03; H, 4.56; N, 11.66.

EXAMPLE 44

1-acetyl-5-fluoro-3-(1-methyl-1,2,3,6-tetrahydropyridin-4-yl)-1H-indole

To a mixture of 0.90 gm (3.94 mMol) 5-fluoro-3-(1-methyl-1,2,3,6-tetrahydropyridin-4-yl)-1H-indole in 20 mL dimethylformamide were added 0.17 gm (4.3 mMol) sodium hydride (60% dispersion in mineral oil). The mixture was stirred for one hour at room temperature at which time 0.47 mL (5.0 mMol) acetic anhydride were added. The reaction mixture was then concentrated under reduced pressure and the residue partitioned between chloroform and water. The organic phase was separated, dried over sodium sulfate and concentrated under reduced pressure. The residue was subjected to flash silica gel chromaography, eluting with chloroform containing 5% methanol. Fractions containing product were combined and concentrated under reduced pressure to give 0.92 gm (86%) of the title compound as a faintly yellow crystalline solid.

m.p.=126°–128° C.

MS(FD): m/e=272 (M$^+$)

EA: Calculated for: $C_{16}H_{17}NOF$: Theory: C, 70.56; H. 6.29; N, 10.29. Found: C, 70.76; H, 6.27; N, 10.34.

EXAMPLE 45

1-methyl-6-chloro-3-(1,2,3,6-tetrahydropyridin-4-yl)-1H-indole

Following the reaction conditions described in Preparation I, 5.0 gm (21.5 mMol) 6-chloro-3-(1,2,3,6- tetrahydropyridin-4-yl)-1H-indole were converted to 6-chloro-3-(1-tert-butoxycarbonyl-1,2,3,6-tetrahydropyridin-4-yl)-1H-indole.

The crude product from the previous reaction was dissolved in 100 mL acetonitrile and then treated with 3 equivalents of iodomethane and 3 equivalents of potassium carbonate. The resulting mixture was heated to reflux for 18 hours. The reaction mixture was then cooled to room temperature, concentrated under reduced pressure and the residue partitioned between chloroform and water. The organic phase was dried over sodium sulfate and concentrated under reduced pressure to give 4.8 gm 1-methyl-6-chloro-3-(1-tert-butoxycarbonyl-1,2,3,6-tetrahydropyridin-4-yl)-1H-indole.

The product was deprotected by dissolving the crude material in 20 mL trifluoroacetic acid. The reaction mixture was immediately poured into water, the solution adjusted to a pH of about 11 by the addition of 1N sodium hydroxide, and the resulting mixture extracted well with chloroform. Organic phases were combined, dried over sodium sulfate and concentrated under reduced pressure. The resultant residue was subjected to flash silica gel chromatography, eluting with chloroform containing 15% methanol. Fractions containing product were combined and concentrated under reduced pressure to give 1.7 gm (32%) of the title compound.

m.p.=100°–103° C.

MS(FD): m/e=246 (M$^+$)

EA: Calculated for: $C_{14}H_{15}N_2Cl$: Theory: C, 68.15; H, 6.13; N, 11.33. Found: C, 67.96; H, 6.15; N, 11.58.

EXAMPLE 46

6-chloro-3-(1-(2-(1-methylpyrazol-4-yl)ethyl) piperidin-4-yl)-1H-indole oxalate

To a mixture of 2.0 gm (8.5 mMol) 6-chloro-3-(piperidin-4-yl)-1H-indole and 2.25 gm (21 mMol) sodium carbonate in 20 mL dimethylformamide was added a solution of 1.74 gm (8.4 mMol) 1-methyl-4-(2-methanesulfonyloxy)ethyl-1H-pyrazole in a minimal volume of dimethylformamide. The resultant mixture was heated at 100° C. for 18 hours. The reaction mixture was then cooled to room temperature and concentrated under reduced pressure. The residue was partitioned between dichloromethane and water. The organic phase was separated and washed first with water and then with saturated aqueous sodium chloride. The remaining organics were dried over sodium sulfate and concentrated under reduced pressure to give a yellow oil. This residue was subjected to silica gel chromatography, eluting with dichloromethane containing 5% methanol. Fractions shown to contain product were combined and concentrated under reduced pressure to give 1.74 gm (59.8%) of 6-chloro-3-(1-(2-(1-methylpyrazol-4-yl)ethyl)piperidin-4-yl)-1H-indole as a yellow foam. The oxalate salt was formed and crystallized from methanol to provide the title compound as yellow crystals.

m.p.=216° C. (dec.)

MS(FD): m/e=342 (M$^+$)

EA: Calculated for: $C_{19}H_{23}N_4Cl.C_2H_2O_4$: Theory: C, 58.27; H, 5.82; N, 12.94. Found: C, 58.15; H, 6.07; N, 13.12.

EXAMPLE 47

6-chloro-3-(1-(2-(1-isopropylpyrazol-4-yl)ethyl) piperidin-4-yl)-1H-indole oxalate Following the procedure described in detail in Example 46, 2.0 gm (8.5 mMol) 6-chloro-3-(piperidin-4-yl)-1H-indole and 1.97 gm (8.5 mMol) 1-isopropyl-4-(2-methanesulfonyloxy)ethyl-1H-pyrazole were combined to provide 1.53 gm (39.1%) of the title compound as a yellow foam.

m.p.=109° C.

MS(FD): m/e=370 (M$^+$)

EA: Calculated for: $C_{21}H_{27}N_4Cl.C_2H_2O_4$: Theory: C, 59.93; H, 6.34; N, 12.15. Found: C, 60.13; H, 6.41; N, 11.92.

EXAMPLE 48

6-chloro-3-(1-(2-(1-phenylpyrazol-4-yl)ethyl) piperidin-4-yl)-1H-indole oxalate

Following the procedure described in detail in Example 46, 2.0 gm (8.5 mMol) 6-chloro-3-(piperidin-4-yl)-1H-indole and 2.26 gm (8.5 mMol) 1-phenyl-4-(2-methanesulfonyloxy)ethyl-1H-pyrazole were combined to provide 2.41 gm (57.3%) of the title compound as a light brown solid.

m.p.=215°–217° C.

MS(FD): m/e=404 (M$^+$)

EA: Calculated for: $C_{24}H_{25}N_4Cl.C_2H_2O_4$: Theory: C, 63.09; H, 5.50; N, 11.32. Found: C, 62.80; H, 5.55; N, 11.30.

EXAMPLE 49

N-(2-pyridinyl)-2-(4-(6-chloro-1H-indol-3-yl)-1,2,3,6-tetrahydropyridin-1-yl)acetamide A mixture of 5.0 gm (21.5 mMol) 6-chloro-3-(1,2,3,6-tetrahydropyridin-4-yl)-1H-indole, 4.0 gm (23.6 mMol) N-(2-pyridinyl)-2-chloroacetamide and 4.45 gm (32 mMol) potassium carbonate in 25 mL dimethylformamide were heated to about 90° C. for 2 hours under nitrogen. The reaction mixture was concentrated under reduced pressure and was then partitioned between chloroform and water. The organic phase was separated, washed sequentially with water and saturated aqueous sodium chloride, dried over sodium sulfate and concentrated under reduced pressure. The residue was crystallized from ethanol to give 2.4 gm (30.4%) of the title compound as a yellow solid.

m.p.=202°–204° C.

MS(FD): m/e=366.2 (M$^+$)

EXAMPLE 50

6-chloro-3-(1-(2-(N-cyclohexylcarbonyl-N-(2-pyridinyl)amino)ethyl)-1,2,3,6-tetrahydropyridin-4-yl)-1H-indole 6-chloro-3-(1-(2-(N-(2-pyridinyl)amino)ethyl)-1,2,3,6-tetrahydropyridin-4-yl)-1H-indole A solution of 0.83 gm (2.28 mMol) N-(2-pyridinyl)-2-(4-(6-chloro-1H-indol-3-yl)-1,2,3,6-tetrahydropyridin-1-yl) acetamide in 20 mL tetrahydrofuran was added dropwise to a slurry of 0.130 gm (3.41 mMol) lithium aluminum hydride in 10 mL tetrahydrofuran at 0° C. at such a rate as to maintain the reaction temperature >5° C. The reaction mixture was then allowed to warm to room temperature over 2 hours. The reaction mixture was then quenched by the sequential addition of water, 15% aqueous sodium hydroxide, and water with vigorous stirring. The resulting slurry was filtered through a bed of celite and the filtrate concentrated under reduced pressure. The residue was subjected to silica gel chromatography, eluting with a chloroform gradient containing 5–8% methanol. Fractions containing product were combined and concentrated under reduced pressure to provide 0.31 gm (39%) of the desired compound.

MS(FD): m/e 352 (M+)

Acylation

A solution of 0.246 gm (0.70 mMol) 6-chloro-3-(1-(2-(N-(2-pyridinyl)amino)ethyl)-1,2,3,6-tetrahydropyridin-4-yl)-1H-indole and 0.146 mL (1.05 mMol) triethylamine in 20 mL dichloromethane was cooled to 0° C. To this solution were then added 0.112 mL (0.84 mMol) cyclohexanecarbonyl chloride and the reaction mixture stirred for 10 minutes. The reaction mixture was then partitioned between water and dichloromethane. The organic phase was dried over sodium sulfate and concentrated under reduced pressure. The residue was subjected to flash silica gel chromatography, eluting with chloroform containing 10% methanol. Fractions shown to contain product were combined and concentrated under reduced pressure to give 0.11 gm (34%) of the title compound as a pale yellow solid.

m.p.=217°–219° C.

MS(FD): m/e=462 (M−1)

EA: Calculated for: $C_{27}H_{31}N_4OCl$: Theory: C, 70.04; H, 6.75; N, 12.16. Found: C, 69.79; H, 6.80; N, 11.87.

EXAMPLE 51

5-chloro-3-(1,2,3,6-tetrahydropyridin-4-yl) benzothiophene hydrochloride 5-chloro-3-(4-hydroxy-1-(tert-butoxycarbonyl)-piperidin-4-yl)benzothiophene A solution of 1.55 mL (1.86 mMol) n-butyllithium in 5.0 mL diethyl ether was cooled to −78° C. under a nitrogen atmosphere. To this cooled solution was added a solution of 0.418 gm (1.68 mMol) 3-bromo-5-chlorobenzothiophene in 10.0 mL diethyl ether. The reaction mixture was stirred at −78° C. for 1 hour and then to it was added dropwise a solution of 0.401 gm (2.0 mMol) 1-tert-butoxycarbonyl-4-piperidone in 5.0 mL diethyl ether. The reaction was stirred an additional 2 hours at −78° C. and was then gradually warmed to −20° C. over 55 minutes. The reaction mixture was then quenched with saturated aqueous sodium bicarbonate, diluted with additional diethyl ether and the phases separated. The organic phase was washed with saturated aqueous sodium chloride, dried over sodium sulfate and concentrated under reduced pressure. The residue was subjected to flash silica chromatography, eluting with toluene containing 10% ethyl acetate. Fractions shown to contain product were combined and concentrated under reduced pressure to give 0.36 gm (58.4%) of the desired compound as a colorless foam.

MS(FD): m/e=367 (M+)

Dehydration/deprotection

To a solution of 0.32 gm (0.86 mMol) 5-chloro-3-(4-hydroxy-1-(tert-butoxycarbonyl)piperidin-4-yl) benzothiophene in 3.0 mL dichloromethane were added 2.0 mL trifluoroacetic acid. The reaction mixture was stirred for 4 hours at room temperature and was then concentrated under reduced pressure. The residue was subjected to flash silica gel chromatography, eluting with chloroform containing 5% methanol. Fractions shown to contain product were combined and then concentrated under reduced pressure to give 0.14 gm (64%) of 5-chloro-3-(1,2,3,6-tetrahydropyridin-4-yl)benzothiophene as a foam. This material was dissolved in diethyl ether and the solution was saturated with hydrogen chloride. The resulting solution was concentrated under reduced pressure to give the title compound as an orange solid.

m.p.=230°–235° C.

MS(FD): m/e=250 (M+)

EA: Calculated for: $C_{13}H_{12}NSCl.HCl$: Theory: C, 54.55; H, 4.58; N, 4.89. Found: C, 54.81; H, 4.77; N, 5.14.

EXAMPLE 52

5-chloro-2-(1,2,3,6-tetrahydropyridin-4-yl) benzothiophene oxalate 5-chloro-2-(4-hydroxy-1-(tert-butoxycarbonyl)piperidin-4-yl)benzothiophene A solution of 0.60 gm (3.56 mMol) 5-chlorobenzothiophene 1.55 mL in 20 mL freshly distilled tetrahydrofuran was cooled to −78° C. under a nitrogen atmosphere. To this was then added a solution of 2.94 mL (3.56 mMol) n-butyllithium and the reaction mixture was stirred at −78° C. for 1 hour. To the resulting anion solution was added dropwise a solution of 0.779 gm (3.91 mMol) 1-tert-butoxycarbonyl-4-piperidone and then the reaction mixture was allowed to warm to 0° C. The reaction mixture was then quenched with saturated aqueous sodium bicarbonate, diluted with 1:1 hexanes:diethyl ether and the phases separated. The organic phase was washed with saturated aqueous sodium chloride, dried over sodium sulfate and concentrated under reduced pressure. The residue was subjected to flash silica chromatography, eluting with toluene containing 10% ethyl acetate. Fractions shown to contain product were combined and concentrated under reduced pressure to give 1.09 gm of the desired compound as a colorless foam contaminated with 20% 1-tert-butoxycarbonyl-4-piperidone.

MS(FD): m/e=367 (M+)

Dehydration/deprotection

A solution of 0.998 gm (2.72 mMol) 5-chloro-2-(4-hydroxy-1-(tert-butoxycarbonyl)piperidin-4-yl) benzothiophene in 10.0 mL dichloromethane was subjected to the reaction conditions described in the previous example, providing 0.444 gm (65%) of 5-chloro-2-(1,2,3,6-tetrahydropyridin-4-yl)benzothiophene as a tan solid. This material was dissolved in ethyl acetate and the solution was treated with oxalic acid. The resulting solution was concentrated under reduced pressure to give the title compound.

m.p.=235°–237° C.

MS(FD): m/e=250 (M+)

EA: Calculated for: $C_{13}H_{12}NSCl.C_2H_2O_4$: Theory: C, 53.02; H, 4.15; N, 4.12. Found: C, 53.06; H, 4.27; N, 4.10.

EXAMPLE 53

4-chloro-, and 6-chloro-2-(1,2,3,6-tetrahydropyridin-4-yl)benzothiophene 4-chloro-2-(4-hydroxy-1-(tert-butoxycarbonyl)piperidin-4-yl)benzothiophene and 6-chloro-2-(4-hydroxy-1-(tert-butoxycarbonyl)piperidin-4-yl)benzothiophene A 1:1 mixture of 4-chlorobenzothiophene and 6-chlorobenzothiophene (1.5 gm, 8.92 mMol, Preparation IV) was subjected to the reaction conditions described in Example 52. Flash silica gel chromatography, eluting with toluene containing 10% ethyl acetate, provided two products.

The first product, 0.66 gm of a colorless solid, was identified by NMR spectroscopy as 4-chloro-2-(4-hydroxy-1-(tert-butoxycarbonyl)piperidin-4-yl)benzothiophene.

MS(FD): m/e=367 (M+)

EA: Calculated for: $C_{18}H_{22}NO_3SCl$: Theory: C, 58.77; H, 6.03; N, 3.81. Found: C, 59.01; H, 6.20; N, 3.87.

The second product, 1.14 gm of a colorless foam, was identified by NMR spectroscopy as 6-chloro-2-(4-hydroxy-1-(tert-butoxycarbonyl)piperidin-4-yl)benzothiophene.

MS(FD): m/e=367 (M+)

EA: Calculated for: $C_{18}H_{22}NO_3SCl$: Theory: C, 58.77; H, 6.03; N, 3.81. Found: C, 58.97; H, 6.08; N, 3.98.

(a) Deprotection/dehydration of the 4-chloro isomer

A solution of 0.29 gm (0.79 mMol) 4-chloro-2-(4-hydroxy-1-(tert-butoxycarbonyl)piperidin-4-yl) benzothiophene in 4.0 mL dichloromethane was subjected to the reaction conditions described in Example 51, providing 0.175 gm (88%) of 4-chloro-2-(1,2,3,6-tetrahydropyridin-4-yl)benzothiophene as a tan powder.

MS(FD): m/e=234 (M$^+$)

(b) Deprotection/dehydration of the 6-chloro isomer

A solution of 1.04 gm (2.83 mMol) 6-chloro-2-(4-hydroxy-1-(tert-butoxycarbonyl)piperidin-4-yl) benzothiophene in 30.0 mL dichloromethane was subjected to the reaction conditions described in Example 51, providing 0.64 gm (90%) of 6-chloro-2-(1,2,3,6-tetrahydropyridin-4-yl)benzothiophene as a tan powder.

MS(FD): m/e=234 (M$^+$)

EXAMPLE 54

5-chloro-2-(1-methyl-1,2,3,6-tetrahydropyridin-4-yl) benzothiophene oxalate 5-chloro-2-(1-methyl-4-hydroxy-1,2,3,6-tetrahydropyridin-4-yl)benzothiophene Subjecting 0.30 gm (1.78 mMol) 5-chlorobenzothiophene and 0.218 gm (1.78 mMol) 1-methyl-4-piperidone to the reaction conditions described in Example 52, 0.321 gm (64%) of 5-chloro-2-(1-methyl-4-hydroxy-1,2,3,6-tetrahydropyridin-4-yl)benzothiophene were recovered as an off-white solid after flash silica gel chromatography (95:5 chloroform:methanol).

MS(FD): m/e=281 (M$^+$)

EA: Calculated for: $C_{14}H_{16}NOSCl$: Theory: C, 59.67; H, 5.72; N. 4.97. Found: C, 58.70; H, 5.36; N, 4.81.

Dehydration

To 0.30 gm (1.06 mMol) 5-chloro-2-(1-methyl-4-hydroxy-1,2,3,6-tetrahydropyridin-4-yl)benzothiophene were added 4.0 mL trifluoroacetic acid. The reaction mixture was stirred for two hours at room temperature. The volatiles were removed under reduced pressure and the residue partitioned between aqueous sodium bicarbonate and dichloromethane. The phases were separated and the organic phase dried over sodium sulfate and then concentrated under reduced pressure. The residue was subjected to flash chromatography, eluting with chloroform containing 5% methanol. Fractions shown to contain product were combined and concentrated under reduced pressure to give 0.336 gm of 5-chloro-2-(1-methyl-1,2,3,6-tetrahydropyridin-4-yl)benzo-thiophene as an orange powder. A portion of this material was dissolved in ethyl acetate and treated with 1.0 equivalents of oxalic acid. The solution was concentrated under reduced pressure to give the title compound as a rust solid.

MS(FD): m/e=264 (M$^+$)

EA: Calculated for: $C_{14}H_{14}NSCl.C_2H_2O_4$: Theory: C, 54.31; H, 4.56; N, 3.96. Found: C, 54.52; H, 4.69; N, 4.17.

EXAMPLE 55

6-methoxy-2-(piperidin-4-yl)benzothiophene monohydrate 6-methoxy-2-(4-hydroxy-1-(tert-butoxycarbonyl)piperidin-4-yl)benzothiophene A solution of 2.49 gm (15.2 mMol) 6-methoxythiophene in 60 mL tetrahydrofuran was subjected to the reaction conditions described in Example 52. Flash silica gel chromatography, eluting with toluene containing 10% ethyl acetate, gave 4.2 gm (76.1%) of the desired compound as a colorless oil.

MS(FD): m/e=363 (M$^+$)

EA: Calculated for: $C_{19}H_{25}NO_4S$: Theory: C, 62.79; H, 6.93; N, 3.85. Found: C, 62.53; H, 6.87; N, 3.85.

Deprotection/dehydration

A solution of 4.2 gm (11.5 mMol) 6-methoxy-2-(4-hydroxy-1-(tert-butoxycarbonyl)piperidin-4-yl) benzothiophene in 40 mL dichloromethane was subjected to the reaction conditions described in Example 51, providing 0.41 gm (14.5%) of the title compound as an orange powder.

MS(FD): m/e=245 (M$^+$)

EA: Calculated for: $C_{14}H_{15}NOS.H_2O$: Theory: C, 63.84; H, 5.69; N, 5.31. Found: C, 63.29; H, 5.97; N, 5.07.

EXAMPLE 56

5-chloro-3-(1-methyl-1,2,3,6-tetrahydropyridin-4-yl) benzothiophene oxalate 5-chloro-3-(1-methyl-4-hydroxypiperidine-4-yl) benzothiophene Subjecting 0.315 gm (1.27 mMol) 3-bromo-5-chlorobenzothiophene and 0.17 mL (1.38 mMol) 1-methyl-4-piperidone to the reaction conditions described in Example 51, 0.28 gm (61%) of 5-chloro-3-(1-methyl-4-hydroxypiperidin-4-yl)benzothiophene were recovered as a colorless solid after flash silica gel chromatography (chloroform containing 10% methanol)

EA: Calculated for: $C_{14}H_{16}NOSCl$: Theory: C, 59.67; H, 5.72; N, 4.97. Found: C, 59.46; H, 5.59; N, 4.78.

Dehydration

A solution of 0.26 gm (0.72 mMol) 5-chloro-3-(1-methyl-4-hydroxypiperidin-4-yl)benzothiophene in 3.0 mL dichloromethane were subjected to the reaction conditions described in Example 51, to provide 0.170 gm (89%) of the title compound as a tan solid.

MS(FD): m/e=263 (M$^+$)

EA: Calculated for: $C_{14}H_{14}NSCl$: Theory: C, 56.00; H, 5.04; N, 4.66. Found: C, 56.21; H, 5.05; N, 4.67.

EXAMPLE 57

5-chloro-2-(1-methylpiperidin-4-yl)benzothiophene

A solution of 0.065 gm (0.25 mMol) 5-chloro-2-(1-methyl-1,2,3,6-tetrahydropyridin-4-yl)benzothiophene was hydrogenated under the conditions previously described to provide 0.017 gm (25%) of the title compound as a slightly colored foam.

EA: Calculated for: $C_{14}H_{16}NSCl$: Theory: C, 63.26; H, 6.07; N, 5.27. Found: C, 63.28; H, 5.92; N, 5.00.

EXAMPLE 58

4-hydroxy-3-(1,2,3,6-tetrahydropyridin-4-yl)-1H-indole

To a solution of 0.30 gm (1.1 mMol) 4-cyclopropylmethoxy-3-(1,2,3,6-tetrahydropyridin-4-yl)-1H-indole in 10 mL acetonitrile were added 0.64 mL (4.4 mMol) trimethylsilyliodide and the reaction mixture was allowed to stir at room temperature for 18 hours. The reaction mixture was concentrated under reduced pressure and the residue partitioned between dilute ammonium hydroxide and ethyl acetate. The phases were separated and the aqueous phase extracted well with ethyl acetate. The organics were combined, washed with saturated aqueous sodium chloride, dried over sodium sulfate and concentrated under reduced pressure. The residue was subjected to radial chromatography, eluting with 15% methanol in dichloromethane containing a trace of ammonium hydroxide. Fractions shown to contain product were combined and concentrated under reduced pressure to provide 0.035 gm (14%) of the title compound as a light tan solid.

MS(FD): m/e=214 (M+)

EXAMPLE 59

4-hydroxy-3-(1-methyl-1,2,3,6-tetrahydropyridin-4-yl)-1H-indole

Following the procedure described in detail in Example 58, 0.300 gm (1.1 mMol) 4-cyclopropylmethoxy-3-(1-methyl-1,2,3,6-tetrahydropyridin-4-yl)-1H-indole were reacted with trimethylsilyl iodide to provide 0.11 gm (44%) of the title compound as a tan solid.

MS(FD): m/e=228 (M+)

EXAMPLE 60

4-hydroxy-3-(1-benzyl-1,2,3,6-tetrahydropyridin-4-yl)-1H-indole

Following the procedure described in detail in Example 58, 1.2 gm (3.35 mMol) 4-cyclopropylmethoxy-3-(1-benzyl-1,2,3,6-tetrahydropyridin-4-yl)-1H-indole were reacted with trimethylsilyl iodide to provide 0.359 gm (35%) of the title compound as a tan solid.

MS(FD): m/e=304 (M+)

EA: Calculated for: $C_{20}H_{20}N_2O$: Theory: C, 78.92; H, 6.62; N, 9.20. Found: C, 78.63; H, 6.70; N, 8.99.

EXAMPLE 61

5-formyl-3-(1-methyl-1,2,3,6-tetrahydropyridin-4-yl)-1H-indole
5-bromo-3-(1-methyl-1,2,3,6-tetrahydropyridin-4-yl)-1H-indole Following the procedure described in detail in Example 1, 30.0 gm (0.153 mole) 5-bromoindole and 38 mL (0.306 mole) 1-methylpiperidone were reacted together to prepare 44.6 gm (100%) of the desired compound as a white solid.

Dianion generation/preparation of aldehyde

A solution of 10.0 gm (34.3 mMol) 5-bromo-3-(1-methyl-1,2,3,6-tetrahydropyridin-4-yl)-1H-indole in 150 mL tetrahydrofuran was added dropwise to a stirring suspension of 7.2 gm (36 mMol) potassium hydride in 150 mL tetrahydrofuran at 0° C. After 30 minutes, the reaction mixture is cooled to −78° C. and to it was added 44.5 mL (75.6 mMol) of a precooled (−78° C.) solution of tert-butyllithium (1.7M in tetrahydrofuran) via cannula. After 15 minutes 4.0 mL (51.5 mL) dimethylformamide was added via cannula and the reaction mixture was allowed to warm slowly to room temperature. The reaction mixture was quenched by the addition of 5N sodium hydroxide and the reaction mixture extracted well with diethyl ether. The organic extracts were combined, washed with saturated aqueous sodium chloride and concentrated under reduced pressure. The resulting residue was subjected to silica gel chromatography, eluting with 4% methanol in dichloromethane. Fractions shown to contain product were combined and concentrated under reduced pressure to provide 3.8 gm (46%) of the title compound as a light yellow solid.

MS(FD): m/e=240 (M+)

EA: Calculated for: $C_{15}H_{16}N_2O$: Theory: C, 74.97; H, 6.71; N, 11.66. Found: C, 74.84; H, 6.89; N, 11.39.

EXAMPLE 62

2-(1-benzyl-4-hydroxypiperidin-4-yl)-1H-indole
1-phenylsulfonyl-1H-indole

A solution of 5.0 gm (42.7 mMol) indole in 60 mL tetrahydrofuran was cooled to −78° C. and to it was added a solution of 28 mL (44.8 mMol) n-butyllithium (1.6M in hexane) via syringe. The cooling bath was removed and the reaction mixture stirred for 1 hour. At this point the reaction mixture was again cooled to −78° C. and to it was added 6.5 mL phenylsulfonyl chloride. The reaction mixture was then to warm to room temperature over 18 hours. The reaction mixture was then partitioned between saturated aqueous sodium bicarbonate and diethyl ether. The phases were separated and the organic phase washed with saturated aqueous sodium chloride, dried over sodium sulfate and concentrated under reduced pressure to provide 7.85 gm (71%) of the desired compound as a white solid.

1-phenylsulfonyl-2-(1-benzyl-4-hydroxypiperidin-4-yl)-1H-indole

A solution of lithium diisopropylamide (15.5 mMol in tetrahydrofuran) was added via cannula to a solution of 4.0 gm (15.5 mMol) 1-phenylsulfonyl-1H-indole in 100 mL tetrahydrofuran at −78° C. The reaction mixture was stirred at this temperature for 1.5 hours, warmed to room temperature for 1 hour and then cooled again to −78° C. To this solution was then added a solution of 2.94 mL (15.9 mMol) 1-benzyl-4-piperidinone in tetrahydrofuran and the resulting mixture was allowed to warm to room temperature over 18 hours. The reaction mixture was then partitioned between saturated aqueous sodium bicarbonate and diethyl ether. The phases were separated and the organic phase washed with saturated aqueous sodium chloride, dried over sodium sulfate and concentrated under reduced pressure. The residue was subjected to silica gel chromatography, eluting with a dichloromethane gradient containing 0–2% methanol. Fractions shown to contain product were combined and concentrated under reduced pressure to provide 3.23 gm (47%) of the desired compound as an off-white solid.

Deprotection

A solution of 1.423 gm (3.2 mMol) 1-phenylsulfonyl-2-(1-benzyl-4-hydroxypiperidin-4-yl)-1H-indole in 60 mL ethanol containing 15 mL 2N sodium hydroxide was heated at reflux until the disappearance of starting material as measured by thin layer chromatography. The reaction mixture was cooled to room temperature and concentrated under reduced pressure. The residue was partitioned between ethyl acetate and 2N sodium hydroxide. The phases were separated and the organic phase was washed with saturated aqueous sodium chloride, dried over sodium sulfate and concentrated under reduced pressure. The residue was subjected to silica gel chromatography, eluting with a dichloromethane gradient containing 0–1.5% methanol. Fractions shown to contain product were combined and concentrated under reduced pressure to provide 0.306 gm (31%) of the title compound.

m.p.=184°–186° C.

MS(FD): m/e=306 (M+)

EA: Calculated for: $C_{20}H_{22}N_2O$: Theory: C, 78.40; H, 7.24; N, 9.14. Found: C, 78.18; H, 7.10; N, 9.01.

EXAMPLE 63

1-phenylsulfonyl-2-(1-benzyl-1,2,3,6-tetrahydropyridin-4-yl)-1H-indole oxalate

A mixture of 1.4 gm (3.1 mMol) 1-phenylsulfonyl-2-(1-benzyl-4-hydroxypiperidin-4-yl)-1H-indole and 1.2 gm (6.2 mMol) p-toluenesulfonic acid in 30 mL toluene was heated at reflux for 18 hours. The reaction mixture was concentrated under reduced pressure and the residue partitioned between ethyl acetate and 2N sodium hydroxide. The phases were separated and the organic phase washed with saturated aqueous sodium chloride, dried over sodium sulfate and concentrated under reduced pressure. The residue was subjected to silica gel chromatography, eluting with 2% methanol in dichloromethane. Fractions shown to contain product were combined and concentrated under reduced pressure to provide 1.13 gm (84%) 1-phenylsulfonyl-2-(1-benzyl-1,2,3, 6-tetrahydropyridin-4-yl)-1H-indole as an off-white foam. A portion was converted to the title compound by treatment with oxalic acid.

m.p.=227°–229° C.

MS(FD): m/e=428 (M$^+$)

EA: Calculated for: $C_{26}H_{24}N_2O_2S \cdot C_2H_2O_4$: Theory: C, 64.85; H, 5.05; N, 5.40. Found: C, 64.96; H, 4.88; N, 5.22.

EXAMPLE 64

2-(piperidin-4-yl)-1H-indole oxalate
2-(1-benzyl-1,2,3,6-tetrahydropyridin-4-yl)-1H-indole A solution of 1.05 gm (2.5 mMol) 1-phenylsulfonyl-2-(1-benzyl-1,2,3,6-tetrahydropyridin-4-yl)-1H-indole in 60 mL ethanol containing 15 mL 2N sodium hydroxide was heated at reflux for 18 hours. The reaction mixture was cooled to room temperature and concentrated under reduced pressure. The residue was partitioned between ethyl acetate and 2N sodium hydroxide. The phases were separated and the organic phase was washed with saturated aqueous sodium chloride, dried over sodium sulfate and concentrated under reduced pressure. The residue was subjected to silica gel chromatography, eluting with dichloromethane containing 2% methanol. Fractions shown to contain product were combined and concentrated under reduced pressure to provide 0.521 gm (74%) of the desired compound as a light tan solid.

Hydrogenation/hydrogenolysis

A mixture of 0.521 gm (1.8 mMol) 2-(1-benzyl-1,2,3,6-tetrahydropyridin-4-yl)-1H-indole and 0.1 gm 5% palladium on carbon were stirred together in ethanol under hydrogen (1 atm) for 48 hours. The reaction mixture was filtered through a bed of celite and the filtrate concentrated under reduced pressure. The residue was subjected to silica gel chromatography, eluting with 20% methanol in dichloromethane containing a trace of ammonium hydroxide. Fractions containing product were combined and concentrated under reduced pressure to provide 0.107 gm (30%) 2-(piperidin-4-yl)-1H-indole as a light yellow solid. A portion of this material was treated with oxalic acid to provide the title compound.

MS(FD): m/e=200 (M$^+$)

EA: Calculated for: $C_{13}H_{16}N_2 \cdot C_2H_2O_4$: Theory: C, 62.06; H. 6.25; N, 9.65. Found: C, 63.12; H, 6.42; N, 9.38.

EXAMPLE 65

5-chloro-2-(piperidin-4-yl)-1H-indole

A mixture of 0.60 gm (3.4 mMol) 4-chlorophenylhydrazine hydrochloride and 0.54 mL (6.7 mMol) pyridine in 20 mL ethanol were stirred at 60° C. for 15 minutes. To this mixture was then added 4-acetylpiperidine hydrochloride and the reaction mixture was stirred for 2 hours at 70° C. The reaction mixture was concentrated under reduced pressure and the residue was treated with polyphosphoric acid. This mixture was heated at 90°–100° C. for 48 hours. The reaction mixture was quenched with a slurry of ice in 5N sodium hydroxide. The aqueous mixture was extracted well with ethyl acetate. The organic phases were combined, washed with saturated aqueous sodium chloride, dried over sodium sulfate and concentrated under reduced pressure. The residue was subjected to silica gel chromatography, eluting with a dichloromethane gradient containing 4–20% methanol. Fractions containing product were combined and concentrated under reduced pressure to provide 0.26 gm (36%) of the title compound as a tan solid.

MS(FD): m/e=234 (M$^+$)

EA: Calculated for: $C_{13}H_{15}N_2Cl$: Theory: C, 66.52; H, 6.44; N, 11.93. Found: C, 66.24; H, 6.34; N, 11.73.

EXAMPLE 66

6-chloro-3-(4-hydroxypiperidin-4-yl)-1H-indole

A mixture of 2.0 gm (13.2 mMol) 6-chloroindole and 4.06 gm (26.3 mMol) 4-piperidinone in 30 mL ethanol which contained 2.21 gm (39.6 mMol) potassium hydroxide was stirred at room temperature for 48 hours. Water (50 mL) was added dropwise to the reaction mixture over 30 minutes. The reaction mixture was allowed stir an additional 2 hours and the solid which formed was collected by filtration to provide a sticky orange solid. A portion of the solid was triturated with acetonitrile and filtered, washed with diethyl ether and dried under reduced pressure to provide 0.254 gm (7.4%) of the title compound as a colorless powder.

MS(FD): m/e=250 (M$^+$)

EXAMPLE 67

5-chloro-2-(4-hydroxy-1-methylpiperidin-4-yl) benzothiophene

A solution of 0.300 gm (1.78 mMol) 5-chlorobenzothiophene in 20 mL tetrahydrofuran was cooled to −78° C. To the cooled solution was then added 1.27 mL (1.78 mMol) n-butyllithium (1.2M in tetrahydrofuran) and the reaction mixture stirred for 1 hour after the addition was complete. To this solution was added 0.218 mL (1.78 mMol) 1-methyl-4-piperidone and the reaction mixture was allowed to warm to 0° C. The reaction mixture was quenched with saturated aqueous sodium bicarbonate and partitioned by the addition of hexane/diethyl ether. The organic phase was washed with saturated aqueous sodium chloride, dried over sodium sulfate and concentrated under reduced pressure to provide 0.34 gm of a tan solid. This residue was subjected to silica gel chromatography, eluting with chloroform containing 5% methanol. Fractions containing product were combined and concentrated under reduced pressure to provide 0.34 gm (68%) of the title compound as an off-white solid.

MS(FD): m/e=281 (M$^+$)

EXAMPLE 68

4-chloro- and 6-chloro-2-(4-hydroxy-1-methylpiperidin-4-yl)benzothiophene

Beginning with 1.0 gm (5.95 mMol) of a 1:1 mixture of 4-chloro- and 6-chlorobenzothiophene, 1.03 gm (61%) of the title compounds were recovered as a slightly colored solid by the procedure described in Example 67.

MS(FD): m/e=281 (M$^+$)

EA: Calculated for: $C_{14}H_{16}NOSCl$: Theory: C, 59.67; H, 5.72; N, 4.97. Found: C, 59.86; H, 5.60; N, 4.97.

EXAMPLE 69

6-chloro-3-(4-hydroxy-1-methylpiperidin-4-yl) benzothiophene

A solution of 0.82 mL (0.98 mMol) n-butyllithium in 5.0 mL diethyl ether was cooled to −78° C. under a nitrogen atmosphere. To this cooled solution was added a solution of 0.22 gm (0.89 mMol) 3-bromo-6-chlorobenzothiophene in 10.0 mL diethyl ether. The reaction mixture was stirred at −78° C. for 1 hour and then to it was added dropwise a solution of 0.12 mL (0.98 mMol) 1-methyl-4-piperidone in 5.0 mL and the reaction was stirred an additional 2 hours at −78° C., then was warmed to −20° C. over 55 minutes. The reaction mixture was then quenched with saturated aqueous sodium bicarbonate, diluted with additional diethyl ether and the phases separated. The organic phase was washed with saturated aqueous sodium chloride, dried over sodium sulfate and concentrated under reduced pressure. The residue was subjected to flash silica chromatography, eluting with toluene containing 10% ethyl acetate. Fractions shown to contain product were combined and concentrated under reduced pressure to give 0.07 gm (25%) of the title compound as a colorless solid.

MS(FD): m/e=281 (M$^+$)

EA: Calculated for: $C_{14}H_{16}NOSCl$: Theory: C, 59.67; H, 5.72; N, 4.97. Found: C, 59.55; H, 6.02; N, 4.87.

EXAMPLE 70

5-chloro-3-(4-hydroxy-1-methylpiperidin-4-yl) benzothiophene

Beginning with 0.315 gm (1.27 mMol) 3-bromo-5-chlorobenzothiophene, 0.28 gm (61%) of the title compound were recovered by the procedure of Example 69.

EA: Calculated for: $C_{14}H_{16}NOSCl$: Theory: C, 59.67; H, 5.72; N. 4.97. Found: C, 59.46; H, 5.59; N, 4.78.

EXAMPLE 71

4-chloro- and 6-chloro-2-(1-methyl-1,2,3,6-tetrahydropyr-idin-4-yl)benzothiophene To a solution of 0.95 gm (3.38 mMol) of a mixture of 4-chloro- and 6-chloro-2-(4-hydroxy-1-methylpiperidin-4-yl)benzothiophene in 20 mL dichloromethane was added 2.6 mL (33.8 mMol) trifluoroacetic acid at 0° C. After stirring for 6 hours the reaction mixture was concentrated under reduced pressure. The residue was dissolved in dichloromethane and this solution washed with saturated aqueous sodium bicarbonate. The remaining organics were dried over sodium sulfate and concentrated under reduced pressure. The residue was subjected to flash silica gel chromatography, eluting with chloroform containing 5% methanol. Fractions containing product were combined and concentrated under reduced pressure to provide 0.82 gm (89%) of the title compounds as a mixture.

MS(FD): m/e=263 (M$^+$)

EA: Calculated for: $C_{14}H_{14}NSCl$: Theory: C, 63.74; H, 5.35; N, 5.31. Found: C, 63.47; H, 5.13; N, 5.18.

EXAMPLE 72

6-chloro-3-(1,2,3,6-tetrahydropyridin-4-yl) benzothiophene

Beginning with 0.41 gm (1.10 mMol) 6-chloro-3-(4-hydroxy-1-(tert-butoxycarbonyl)piperidin-4-yl)benzothiophene, the title compound was prepared by the procedure of Example 71.

HRMS: Calculated for: $C_{13}H_{12}NSCl$: Theory: 250.0457. Found: 250.0460.

EXAMPLE 73

4-chloro-2-(piperidin-4-yl)benzothiophene tetrahydrate

To a solution of 0.36 gm (0.98 mMol) 4-chloro-2-(1-tert-butoxycarbonyl-4-hydroxypiperidin-4-yl) in 1.56 mL trifluoroacetic acid were added 0.755 mL (9.8 mMol) triethylsilane and the mixture was stirred at 60° C. for 18 hours. The reaction mixture was then cooled to room temperature and concentrated under reduced pressure. The remaining oil was diluted with ethyl acetate and the resulting solution extracted twice with saturated aqueous sodium bicarbonate and twice with saturated aqueous sodium chloride. The remaining organics were dried over sodium sulfate and concentrated under reduced pressure. The residual oil was subjected to silica gel chromatography, eluting with 10% methanol in chloroform. Fractions containing product were combined and concentrated under reduced pressure to provide 0.19 gm (77%) of the title compound.

MS(FD): m/e=251 (M$^+$)

EA: Calculated for: $C_{13}H_{14}NSCl \cdot 4H_2O$: Theory: C, 48.22; H, 4.32; N, 4.32. Found: C, 48.37; H, 4.40; N, 4.14.

EXAMPLE 74

5-(4,5-dihydrothiazol-5-yl)-3-(1-methyl-1,2,3,6-tetrahydropyridin-4-yl)-1H-indole A mixture of 1.0 gm (4.2 mMol) 5-cyano-3-(1-methyl-1,2,3,6-tetrahydropyridin-4-yl)-1H-indole and 0.90 gm (11.7 mMol) 2-mercaptoethylamine in 20 mL ethanol was heated to reflux for 18 hours. The reaction mixture was cooled to room temperature and a colorless crystalline solid formed. The solid was isolated by filtration, washed with ethanol and dried under reduced pressure to provide 0.64 gm (51%) of the title compound.

m.p.=260°–263° C.

MS(FD): m/e=297 (M$^+$)

EA: Calculated for: $C_{17}H_{19}N_3S$: Theory: C, 68.65; H, 6.44; N. 14.13. Found: C, 68.74; H, 6.58; N, 14.24.

EXAMPLE 75

5-(4,5-dihydrothiazol-5-yl)-3-(1-methylpiperidin-4-yl)-1H-indole

To a mixture of 0.54 gm (1.8 mMol) 5-(4,5-dihydrothiazol-5-yl)-3-(1-methyl-1,2,3,6-tetrahydropyridin-4-yl)-1H-indole in 20 mL trifluoroacetic acid were added slowly 320 μL (2 mMol) triethylsilane. The reaction mixture was stirred at room temperature for 18 hours and then concentrated under reduced pressure. The residual oil was partitioned between ethyl acetate and aqueous potassium carbonate. The organic phase was dried over sodium sulfate and concentrated under reduced pressure. The residue was crystallized from acetonitrile to provide 0.40 gm (74%) of the title compound compound as a crystalline solid.

m.p.=158°–160° C.

MS(FD): m/e=299 (M$^+$)

EA: Calculated for: $C_{17}H_{21}N_3S$: Theory: C, 68.19; H, 7.07; N, 14.03. Found: C, 68.34; H, 7.09; N, 14.05.

The efficacy of the compounds of Formula I to inhibit the reuptake of serotonin has been determined by a paroxetine binding essay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32M sucrose and 20 μM glucose. The preparations were resuspended after centrifugation by homogenizing in 50 volumes of cold reaction medium (50 μM sodium chloride, 50 μM potassium chloride, pH 7.4) and centrifuging at 50,000 g for 10 minutes. The process was repeated two times with a 10-minute incubation at 37° C. between the second and third washes. The resulting pellet was stored at −70° C. until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 μg protein/tube). Samples were incubated at 37° C. for 30 minutes; those containing 1 μM fluoxetine were used to determine nonspecific binding of $^3$H-paroxetine. After incubation, the tubes were filtered through Whatman GF/B filters, which were soaked in 0.05% polyethylenimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of Formula I by the above method showed potent reuptake activity, in some cases activity in the low nanomolar range.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated. It will be understood that the dosage ranges for other animals will necessarily be quite different from the doses administered to humans, and accordingly that the dosage ranges described below in the section on tobacco withdrawal must be recalculated. For example, a small dog may be only 1/10th of a typical human's size, and it will therefore be necessary for a much smaller dose to be used. The determination of an effective amount for a certain non-human animal is carried out in the same manner described below in the case of humans, and veterinarians are well accustomed to such determinations.

Further, the activity of compounds of Formula I in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula I will be set out in detail below. Again, the effective amount of a compound for the inhibition of serotonin reuptake, or for a specific therapeutic method which depends on the inhibition of reuptake, is determined in the manner described below under the heading of smoking withdrawal.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 52 | 30.0 |
| Starch | 305.0 |
| Magnesium stearate | 5.0 |

The above ingredients are mixed and filled into hard gelatin capsules in 340 mg quantities.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A compound of Formula II:

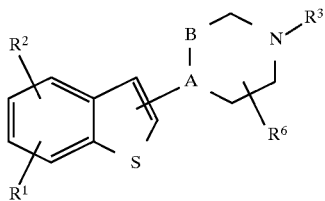

where

A—B is —C($R^5$)—$CH_2$—;

$R^1$ is H, halo, formyl, $C_1$–$C_4$ alkyl, $C_1$–$C_4$ alkoxy, 4,5-dihydrothiazol-2-yl, cyano, nitro, carboxamido, trifluoromethyl or hydroxy;

$R^2$ is H or halo;

$R^3$ is H, $C_1$–$C_4$ alkyl, ($C_1$–$C_4$ alkylene)-aryl, or —$CH_2$—Y—$NR^7R^8$;

$R^5$ is H or OH;

$R^6$ is H or methyl;

Y is —$CH_2$— or —C(O)—;

$R^7$ is pyridinyl; and $R^8$ is H or —C(O)—($C_3$–$C_6$ cycloalkyl), provided that $R^1$ and $R^2$ may not both be H and pharmaceutically acceptable salts and hydrates thereof.

2. A compound of claim 1 where A—B is —C($R^5$)—$CH_2$ and $R^5$ is H.

3. A compound of claim 1 which is of Formula III:

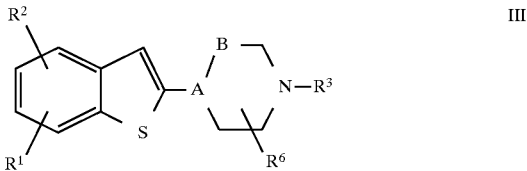

where

A—B is —C($R^5$)—$CH_2$—;

$R^1$ is H, halo, formyl, $C_1$–$C_4$ alkyl, $C_1$–$C_4$ alkoxy, cyano, nitro, carboxamido, trifluoromethyl or hydroxy;

$R^2$ is H or halo;

$R^3$ is H, $C_1$–$C_4$ alkyl, ($C_1$–$C_4$ alkylene)-aryl, or —$CH_2$—Y—$NR^7R^8$;

$R^5$ is H or OH;

$R^6$ is H or methyl;

Y is —$CH_2$— or —C(O)—;

$R^7$ is pyridinyl; and $R^8$ is H or —C(O)-($C_3$–$C_6$ cycloalkyl), provided that $R^1$ and $R^2$ may not both be H.

4. A compound of claim 3 where $R^3$ is H or $C_1$–$C_4$ alkyl.

5. A pharmaceutical composition which comprises, in association with a pharmaceutically acceptable carrier, diluent or excipient, an effective amount of a compound of claim 1.

6. A composition of claim 5, where the compound is of Formula III.

* * * * *